(12) United States Patent
Koike et al.

(10) Patent No.: US 10,792,405 B2
(45) Date of Patent: Oct. 6, 2020

(54) VENTRICULAR ASSIST SYSTEM AND BLOOD PUMP CONTROLLER

(71) Applicant: SUN MEDICAL TECHNOLOGY RESEARCH CORPORATION, Suwa-shi, Nagano (JP)

(72) Inventors: Nozomi Koike, Nagano (JP); Shinji Kobayashi, Nagano (JP); Hideki Kanebako, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 92 days.

(21) Appl. No.: 16/211,188

(22) Filed: Dec. 5, 2018

(65) Prior Publication Data

US 2019/0167873 A1     Jun. 6, 2019

(30) Foreign Application Priority Data

Dec. 6, 2017 (JP) ................. 2017-234222

(51) Int. Cl.
*A61M 1/10*         (2006.01)
*A61M 1/12*         (2006.01)

(52) U.S. Cl.
CPC .......... *A61M 1/1025* (2014.02); *A61M 1/102* (2014.02); *A61M 1/1017* (2014.02); *A61M 1/1031* (2014.02); *A61M 1/1086* (2013.01); *A61M 1/122* (2014.02); *A61M 1/127* (2013.01); *A61M 2205/0216* (2013.01); *A61M 2205/3606* (2013.01); *A61M 2205/366* (2013.01)

(58) Field of Classification Search
None
See application file for complete search history.

(56) References Cited

U.S. PATENT DOCUMENTS

| 2011/0015732 A1* | 1/2011 | Kanebako | A61M 1/1086 623/3.1 |
| 2011/0112354 A1* | 5/2011 | Nishimura | A61M 1/008 600/16 |
| 2013/0102834 A1* | 4/2013 | Kaneshima | F04D 29/046 600/16 |
| 2013/0345804 A1* | 12/2013 | Kanebako | A61M 1/1086 623/3.1 |

(Continued)

FOREIGN PATENT DOCUMENTS

JP     2014-128516 A     7/2014

*Primary Examiner* — Brian T Gedeon
(74) *Attorney, Agent, or Firm* — Hauptman Ham, LLP

(57) ABSTRACT

A ventricular assist system and a blood pump controller including a blood pump usable in a state where a first slide surface and a second slide surface are brought into contact with each other, and a cool sealing liquid is supplied to a gap formed between the first slide surface and the second slide surface; a first sub controller having a first cool sealing liquid reservoir, a cool sealing liquid pump, a first pipe joint upstream side, and a fourth pipe joint downstream side; and a second sub controller having a blood pump drive circuit, a battery, a first pipe joint downstream side, a second pipe joint upstream side, a third pipe joint downstream side, and a fourth pipe joint upstream side. The first sub controller and the second sub controller are detachably connected by a first pipe joint and a fourth pipe joint.

13 Claims, 15 Drawing Sheets

(56) References Cited

U.S. PATENT DOCUMENTS

| | | | | |
|---|---|---|---|---|
| 2015/0297812 A1* | 10/2015 | Miyakoshi | .......... | A61M 1/1005 600/16 |
| 2015/0328384 A1* | 11/2015 | Nishimura | .......... | A61M 1/1086 623/3.28 |
| 2019/0374691 A1* | 12/2019 | Kanebako | ........... | A61M 1/1086 |

* cited by examiner

VENTRICULAR ASSIST SYSTEM AND BLOOD PUMP CONTROLLER

RELATED APPLICATIONS

The present application claims priority to Japanese Application No. 2017-234222 filed Dec. 6, 2017, the disclosure of which is hereby incorporated by reference herein in its entirety.

BACKGROUND OF THE INVENTION

1. Field of the Invention

The present invention relates to a ventricular assist system and a blood pump controller.

2. Description of the Related Art

There has been known a so-called centrifugal type blood pump which supplies blood into a body of a user using a centrifugal force generated by the rotation of an impeller (see JP-A-2014-128516, for example).

FIG. 14A to FIG. 14C are views for describing one example of a centrifugal type blood pump 409. FIG. 14A is a cross-sectional view showing the entire configuration of the blood pump 409. FIG. 14B is a cross-sectional view of a main part showing a portion of FIG. 14A surrounded by a dotted line C in an enlarged manner. FIG. 14C is a plan view of a rotary side slide member 922 taken along a line A-A in FIG. 14B as viewed in an arrow direction. FIG. 15 is a schematic view for describing a conventional ventricular assist system 9 and a conventional blood pump controller 19. FIG. 16 is a block diagram for describing the conventional ventricular assist system 9 and the conventional blood pump controller 19.

As shown in FIG. 14A to FIG. 14C, the centrifugal type blood pump 409 includes: a fixed side slide member 912 having an annular first slide surface 911; a rotary side slide member 922 having an annular second slide surface 921; a blood pump chamber 930 positioned on an outer peripheral side of the fixed side slide member 912 and the rotary side slide member 922; an impeller 923 housed in the blood pump chamber 930 and being integrally rotatable with the rotary side slide member 922 about a rotary axis AX1; a motor 940 capable of imparting rotary energy to the impeller 923; and a cool sealing liquid flow chamber 950a which is positioned on an inner peripheral side of the fixed side slide member 912 and the rotary side slide member 922 and through which a cool sealing liquid L1 supplied from an outside flows. The blood pump 409 is used in a state where the first slide surface 911 and the second slide surface 921 are brought into contact with each other, and the cool sealing liquid L1 is supplied to a gap 954 formed between the first slide surface 911 and the second slide surface 921 from the cool sealing liquid flow chamber 950a.

The cool sealing liquid L1 flows through between a shaft 924 of the motor 940 for imparting a rotational force to the impeller 923 and a fixed portion 910 such as a fixed side slide member 912 (forming a part of a cool sealing liquid flow chamber), and the cool sealing liquid L1 is used for cooling and lubricating the shaft 924 and the fixed portion 910. Further, as described previously, the cool sealing liquid L1 is supplied to a gap 954 formed between the first slide surface 911 of the fixed side slide member 912 and the second slide surface 921 of the rotary side slide member 922 as a sealing liquid thus preventing the intrusion of a blood component into the gap 954 formed between the first slide surface 911 and the second slide surface 921 (also see JP-A-2014-128516).

The conventional ventricular assist system 9 includes: the above-mentioned blood pump 409; the blood pump controller 19 which drives the blood pump 409 and also supplies the cool sealing liquid L1 to the blood pump 409; an electric cable 330 through which a drive signal is transmitted from the blood pump controller 19 to the blood pump 409; an up tube 310 which makes the cool sealing liquid L1 flow from the blood pump controller 19 to the blood pump 409; and a down tube 320 which makes the cool sealing liquid L1 flow from the blood pump 409 to the blood pump controller 19 (see FIG. 15).

The conventional blood pump controller 19 includes: a blood pump drive circuit 962 which is electrically connected to the electric cable 330 and drives the motor 940 of the blood pump 409; a cool sealing liquid reservoir 951 which stores the cool sealing liquid L1; a cool sealing liquid pump 952 which sucks the cool sealing liquid L1 supplied from the cool sealing liquid reservoir 951 and supplies the sucked cool sealing liquid L1; an up pipe joint 971 which is formed of detachably connectable up pipe joint upstream side 971a and up pipe joint downstream side 971b, and relays the cool sealing liquid L1 supplied from the cool sealing liquid pump 952 to the up tube 310; and a down pipe joint 972 which is formed of detachably connectable down pipe joint upstream side 972a and down pipe joint downstream side 972b, and relays the cool sealing liquid L1 supplied from the down tube 320 to the cool sealing liquid reservoir 951 (see FIG. 16).

The conventional ventricular assist system 9 and the blood pump controller 19 have the cool sealing liquid pump 952. With the use of the cool sealing liquid pump 952, a pressure of the cool sealing liquid L1 supplied toward the blood pump 409 (eventually to the gap 954 formed between the first slide surface 911 and the second slide surface 921) can be increased.

The conventional ventricular assist system 9 and the blood pump controller 19 also include the cool sealing liquid reservoir 951. A sufficient amount of cool sealing liquid L1 can be stored in the cool sealing liquid reservoir 951 and hence, even when the cool sealing liquid L1 is excessively consumed in the gap 954 formed between the first slide surface 911 and the second slide surface 921, the cool sealing liquid L1 can be continuously supplied to the gap 954 so that an operation of the blood pump 409 can be continued (a function which the cool sealing liquid reservoir 951 performs).

SUMMARY OF INVENTION

However, it is necessary for the cool sealing liquid pump 952 to ensure considerably large liquid supply ability and it is necessary for the cool sealing liquid reservoir 951 to ensure a considerably large capacity. Accordingly, the cool sealing liquid pump 952, the cool sealing liquid reservoir 951 and the like have considerably large correspondingly size and weight. To be more specific, there has been a case where a diaphragm pump is used as the cool sealing liquid pump 952, and a reservoir which stores 1000 cc of cool sealing liquid L1 which is injection-use water is used as the cool sealing liquid reservoir 951.

Under such a situation, the blood pump controller 19 in which the cool sealing liquid pump 952, the cool sealing liquid reservoir 951 and the like are incorporated also has a considerably large size and weight. Accordingly, when a user of the ventricular assist system who has a heart failure carries the blood pump controller 19 when he goes out, the size and the weight of such a blood pump controller 19 imposes a large burden on the user.

In view of the above, there has been a strong demand for a blood pump controller and a ventricular assist system which impose a small burden on a user and have high portability enabling the user to carry them relatively easily. For example, there has been a demand for a blood pump controller which is so small and light-weighted that the user can use the blood pump controller wearing the blood pump controller.

The present invention has been made in view of the above-mentioned circumstances, and it is an object of the present invention to provide a ventricular assist system and a blood pump controller which impose a small burden on a user and have high portability.

[1] According to the first aspect of the present invention, there is provided a ventricular assist system which includes:

a blood pump having: a fixed side slide member having an annular first slide surface; a rotary side slide member having an annular second slide surface; a blood pump chamber positioned on an outer peripheral side of the fixed side slide member and the rotary side slide member, an impeller housed in the blood pump chamber and being integrally rotatable with the rotary side slide member; a motor capable of imparting rotary energy to the impeller; and a cool sealing liquid flow chamber which is positioned on an inner peripheral side of the fixed side slide member and the rotary side slide member and through which a cool sealing liquid supplied from an outside flows, the blood pump being used in a state where the first slide surface and the second slide surface are brought into contact with each other, and the cool sealing liquid is supplied to a gap formed between the first slide surface and the second slide surface from the cool sealing liquid flow chamber;

a blood pump controller for driving the blood pump and for supplying the cool sealing liquid to the blood pump;

an electric cable for transmitting a drive signal from the blood pump controller to the blood pump;

an up tube through which the cool sealing liquid is made to flow from the blood pump controller to the blood pump; and a down tube through which the cool sealing liquid is made to flow from the blood pump to the blood pump controller, wherein the blood pump controller includes:

a blood pump drive circuit electrically connected to the electric cable and provided for driving the motor of the blood pump;

a battery electrically connected to the blood pump drive circuit for supplying a power source to the blood pump drive circuit;

a first cool sealing liquid reservoir for storing the cool sealing liquid;

a cool sealing liquid pump for sucking the cool sealing liquid supplied from the first cool sealing liquid reservoir and discharging the sucked cool sealing liquid;

a first pipe joint formed of a first pipe joint upstream side and a first pipe joint downstream side which are detachably connected to each other and being capable of relaying the cool sealing liquid supplied from the cool sealing liquid pump;

a second pipe joint formed of a second pipe joint upstream side and a second pipe joint downstream side which are detachably connected to each other where the second pipe joint downstream side is connected to the up tube so as to enable the second pipe joint to relay the cool sealing liquid supplied from the first pipe joint to the up tube;

a third pipe joint formed of a third pipe joint upstream side and a third pipe joint downstream side which are detachably connected to each other where the third pipe joint upstream side is connected to the down tube so as to enable the third pipe joint to relay the cool sealing liquid supplied from the down tube to an inside of the blood pump controller; and a fourth pipe joint formed of a fourth pipe joint upstream side and a fourth pipe joint downstream side which are detachably connected to each other and being capable of relaying the cool sealing liquid supplied from the third pipe joint downstream side to the first cool sealing liquid reservoir, and the blood pump controller includes:

a first sub controller having the first cool sealing liquid reservoir, the cool sealing liquid pump, the first pipe joint upstream side, and the fourth pipe joint downstream side; and a second sub controller having the blood pump drive circuit, the battery, the first pipe joint downstream side, the second pipe joint upstream side, the third pipe joint downstream side, and the fourth pipe joint upstream side, and the first sub controller and the second sub controller are separable from each other and are joinable to each other by detachably connecting the first pipe joint and the fourth pipe joint.

In the ventricular assist system of the present invention, the blood pump controller is formed of: the first sub controller which includes the first cool sealing liquid reservoir, the cool sealing liquid pump, the first pipe joint upstream side, and the fourth pipe joint downstream side; and the second sub controller which includes the blood pump drive circuit, the battery, the first pipe joint downstream side, the second pipe joint upstream side, the third pipe joint downstream side, and the fourth pipe joint upstream side. The first sub controller and the second sub controller are configured to be separable from each other and joinable to each other by detachably connecting the first pipe joint and the fourth pipe joint.

Due to such a configuration, a user can separate the second sub controller from the first sub controller, and can carry only the second sub controller. That is, the user can continue an operation of the blood pump by carrying only the second sub controller without carrying the first sub controller which includes the first cool sealing liquid reservoir and the like which have relatively large weight and volume.

Accordingly, the present invention can provide the ventricular assist system which imposes a small burden on a user and has high portability.

[2] In the ventricular assist system according to the present invention, it is preferable that the first pipe joint upstream side, the first pipe joint downstream side, the fourth pipe joint upstream side, and the fourth pipe joint downstream side respectively include a relay port shut off means which is disposed in a vicinity of a relay port which appears when a pipe joint of each of said respective sides is separated from a pipe joint of a counterpart side which forms a pair with said each of the sides and shuts off between an outer portion and an inner portion of the relay port.

In the ventricular assist system described in the above-mentioned [2], the first pipe joint upstream side, the first pipe joint downstream side, the fourth pipe joint upstream side, and the fourth pipe joint downstream side respectively have the relay port shut off means.

With such a configuration, when a user connects the second sub controller to the first sub controller or removes the second sub controller from the first sub controller or when the user carries the second sub controller, the outside and the inside (the inside of the first sub controller or the second sub controller) in the vicinity of the relay port is shut off from each other by the relay port shut off means and hence, it is possible to prevent the intrusion of foreign substances, germs or the like from the relay port to the inside. Further, it is also possible to prevent a leakage of a cool sealing liquid from the inside. In this manner, an operation of the blood pump can be continued safely and hygienically even after the second sub controller is separated.

[3] In the ventricular assist system according to the present invention, it is preferable that in the blood pump, a dynamic pressure groove be formed on a member which forms a part of a cool sealing liquid flow path.

With such a configuration, fluidity of a cool sealing liquid is accelerated by the dynamic pressure groove and hence, the cool sealing liquid can be more effectively guided to the gap formed between the first slide surface and the second slide surface. Accordingly, the dynamic pressure groove can compensate for a function which the cool sealing liquid pump 952 performs in the conventional ventricular assist system.

[4] In the ventricular assist system according to the present invention, it is preferable that the dynamic pressure groove be a groove formed on the first slide surface of the fixed side slide member or the second slide surface of the rotary side slide member.

According to the present invention, by forming the dynamic pressure groove on at least either one of the first slide surface and the second slide surface which rotate relative to each other, it is possible to impart a dynamic pressure effect to a cool sealing liquid filled in the gap formed between the first slide surface and the second slide surface and hence, it is possible to increase a drawing effect applied to the cool sealing liquid filled in the gap formed between the first slide surface and the second slide surface. As a result, the cool sealing liquid can be more effectively guided to the gap formed between the first slide surface and the second slide surface.

[5] In the ventricular assist system according to the present invention, it is preferable that the dynamic pressure groove be a groove formed on a shaft connected to the motor or a bearing.

According to the present invention, by forming the dynamic pressure groove on at least either one of the shaft and the bearing which rotate relative to each other, it is possible to impart a dynamic pressure effect to a cool sealing liquid which passes through between the shaft and the bearing. As a result, the cool sealing liquid can be more effectively guided to the gap formed between the first slide surface and the second slide surface.

[6] The blood pump controller according to the present invention is the above-mentioned blood pump controller used in the ventricular assist system described in any one of the above-mentioned [1] to [5], and the blood pump controller includes:

the blood pump drive circuit electrically connected to the electric cable and provided for driving the motor of the blood pump;

the battery electrically connected to the blood pump drive circuit for supplying a power source to the blood pump drive circuit;

the first cool sealing liquid reservoir for storing the cool sealing liquid;

the cool sealing liquid pump for sucking the cool sealing liquid supplied from the first cool sealing liquid reservoir and discharging the sucked cool sealing liquid;

the first pipe joint formed of the first pipe joint upstream side and the first pipe joint downstream side which are detachably connected to each other and being capable of relaying the cool sealing liquid supplied from the cool sealing liquid pump;

the second pipe joint formed of the second pipe joint upstream side and the second pipe joint downstream side which are detachably connected to each other where the second pipe joint downstream side is connected to the up tube so as to enable the second pipe joint to relay the cool sealing liquid supplied from the first pipe joint to the up tube;

the third pipe joint formed of the third pipe joint upstream side and the third pipe joint downstream side which are detachably connected to each other where the third pipe joint upstream side is connected to the down tube so as to enable the third pipe joint to relay the cool sealing liquid supplied from the down tube to an inside of the blood pump controller; and the fourth pipe joint formed of the fourth pipe joint upstream side and the fourth pipe joint downstream side which are detachably connected to each other and being capable of relaying the cool sealing liquid supplied from the third pipe joint downstream side to the first cool sealing liquid reservoir, and the first sub controller having the first cool sealing liquid reservoir, the cool sealing liquid pump, the first pipe joint upstream side, the fourth pipe joint downstream side and the second sub controller having the blood pump drive circuit, the battery, the first pipe joint downstream side, the second pipe joint upstream side, the third pipe joint downstream side, and the fourth pipe joint upstream side are separable from each other and are joinable with each other by detachably connecting the first pipe joint and the fourth pipe joint.

In the blood pump controller according to the present invention, the first sub controller which includes the first cool sealing liquid reservoir, the cool sealing liquid pump, the first pipe joint upstream side, and the fourth pipe joint downstream side and the second sub controller which includes the blood pump drive circuit, the battery, the first pipe joint downstream side, the second pipe joint upstream side, the third pipe joint downstream side, and the fourth pipe joint upstream side are configured to be separable from each other and joinable to each other by detachably connecting the first pipe joint and the fourth pipe joint.

Due to such a configuration, a user can separate the second sub controller from the first sub controller, and can carry only the second sub controller. That is, the user can continue an operation of the blood pump by carrying only the second sub controller without carrying the first sub controller which includes the first cool sealing liquid reservoir and the like which have relatively large weight and volume. Accordingly, the present invention can provide the blood pump controller which imposes a small burden on a user and has high portability.

[7] In the blood pump controller according to the present invention, it is preferable that the second sub controller further include a second cool sealing liquid reservoir disposed between the first pipe joint downstream side and the second pipe joint upstream side, having capacity smaller than capacity of the first cool sealing liquid reservoir, and storing the cool sealing liquid.

In the blood pump controller according to the present invention, the second cool sealing liquid reservoir is newly provided between the first pipe joint downstream side and the second pipe joint upstream side in the second sub controller. With such a configuration, a cool sealing liquid stored in the second cool sealing liquid reservoir can also contribute to the supply of the cool sealing liquid to the gap formed between the first slide surface and the second slide surface. Accordingly, even if a consumption amount of the cool sealing liquid between the first slide surface and the second slide surface is increased compared to a usual consumption amount, the cool sealing liquid can be supplied to the gap formed between the first slide surface and the second slide surface over a sufficient period by only the second sub controller and hence, an operation of the blood pump can be continued (unnecessary to frequently replenish the cool sealing liquid).

Further, according to the present invention, the second cool sealing liquid reservoir can compensate for a function which the cool sealing liquid reservoir 951 performs in the conventional ventricular assist system and hence, unlike the prior art, it is unnecessary to carry the whole cool sealing liquid reservoir 951 having a large size and a large weight.

Further, in the present invention, the capacity of the second cool sealing liquid reservoir is set smaller than the capacity of the first cool sealing liquid reservoir. By setting such a capacity ratio between the first cool sealing liquid reservoir and the second cool sealing liquid reservoir, in carrying the ventricular assist system by separating only the second sub controller, a user carries the second cool sealing liquid reservoir having a relatively small capacity compared to the first cool sealing liquid reservoir and hence, a burden imposed on the user can be further reduced.

Accordingly, the present invention can provide the blood pump controller which imposes a small burden on a user and has high portability.

[8] In the blood pump controller according to the present invention, it is preferable that the second sub controller further include a pressure applying means for increasing a pressure of the cool sealing liquid to be supplied to the blood pump.

According to the present invention, a supply pressure of a cool sealing liquid can be positively increased by the pressure applying means and hence, the cool sealing liquid can be more effectively guided between the first slide surface and the second slide surface. Eventually, a state of the cool sealing liquid in the gap formed between the first slide surface and the second slide surface can be brought into a state closer to a preferable state and hence, the blood pump can be operated safely and with certainty.

According to the present invention, the pressure applying means can compensate for a function which the cool sealing liquid pump 952 performs in the conventional ventricular assist system and hence, unlike the prior art, it is unnecessary to carry the cool sealing liquid pump 952 having a large size and a large weight.

[9] In the blood pump controller according to the present invention, it is preferable that the pressure applying means be an elastic member which applies a force to the second cool sealing liquid reservoir.

According to the present invention, by using the elastic member as the pressure applying means, it is possible to acquire the pressure applying means which has small possibility of occurrence of a defect due to the relatively convenient and simple structure.

[10] In the blood pump controller according to the present invention, it is preferable that the pressure applying means be an actuator which applies a force to the second cool sealing liquid reservoir.

According to the present invention, by using the actuator as the pressure applying means, it is possible to acquire the pressure applying means where a magnitude of a pressure, a timing at which a pressure is applied, a time during which the pressure is applied and the like can be flexibly controlled.

[11] In the blood pump controller according to the present invention, it is preferable that the second cool sealing liquid reservoir have a flattened portion, and have a flat external appearance as a whole.

According to the present invention, the second cool sealing liquid reservoir has a flat external appearance as a whole and hence, a size of the second cool sealing liquid reservoir in a thickness direction can be made small whereby a housing of the second sub controller in which the second cool sealing liquid reservoir is housed can be made thin. By making the second sub controller thin, a user can easily carry and hence, the second sub controller has excellent portability.

Further, according to the present invention, the second cool sealing liquid reservoir has the flattened portion and hence, the whole surface of the flattened portion can be pressed by making use of the flattened portion. For example, by merely imparting the slight displacement to the second cool sealing liquid reservoir in a direction perpendicular to the surface of the flattened portion by the pressure applying means, a volume of the second cool sealing liquid reservoir is relatively largely changed and hence, a pressure of a cool sealing liquid to be supplied to the blood pump can be easily increased.

It is preferable to further provide a flat surface plate (pressure applying auxiliary means) which overlaps with the surface of the flattened portion thus applying a force to the second cool sealing liquid reservoir by the pressure applying means by way of the flat surface plate.

[12] In the blood pump controller according to the present invention, it is preferable that the second cool sealing liquid reservoir be formed using a material which contains polypropylene or polyethylene.

According to the present invention, by forming the second cool sealing liquid reservoir using a material which contains polypropylene or polyethylene, it is possible to acquire the second cool sealing liquid reservoir which is relatively easily deformable (that is, a volume of the second cool sealing liquid reservoir easily changes) and can easily convert a force applied from the pressure applying means to a supply pressure of a cool sealing liquid.

A material which contains polypropylene or polyethylene can be easily formable and light-weighted and hence, it is possible to easily form the second cool sealing liquid reservoir having a small thickness and being light-weighted whereby a burden imposed on a user when the user carries the second sub controller can be reduced.

[13] It is preferable that the blood pump controller according to the present invention further include a separation detection means for detecting a separated state and a joined state between the first sub controller and the second sub controller.

By making use of such a separation detection means, for example, the sequence performed after the first sub controller and the second sub controller are separated from each other and the sequence performed after the first sub controller and the second sub controller are joined to each other can be started at appropriate timing.

DESCRIPTION OF PREFERRED EMBODIMENTS

Hereinafter, a ventricular assist system and a blood pump controller according to the present invention are described based on embodiments shown in drawings. The respective drawings are schematic drawings, and do not necessarily strictly reflect actual sizes.

Embodiment 1

1. Configuration of Ventricular Assist System 1 and Blood Pump Controller 11 According to Embodiment 1
(1) Ventricular Assist System 1

The ventricular assist system which compensates for a part of a function of a heart for sustaining the life of a patient (user) until patient receives the heart implantation.

Figure 1:
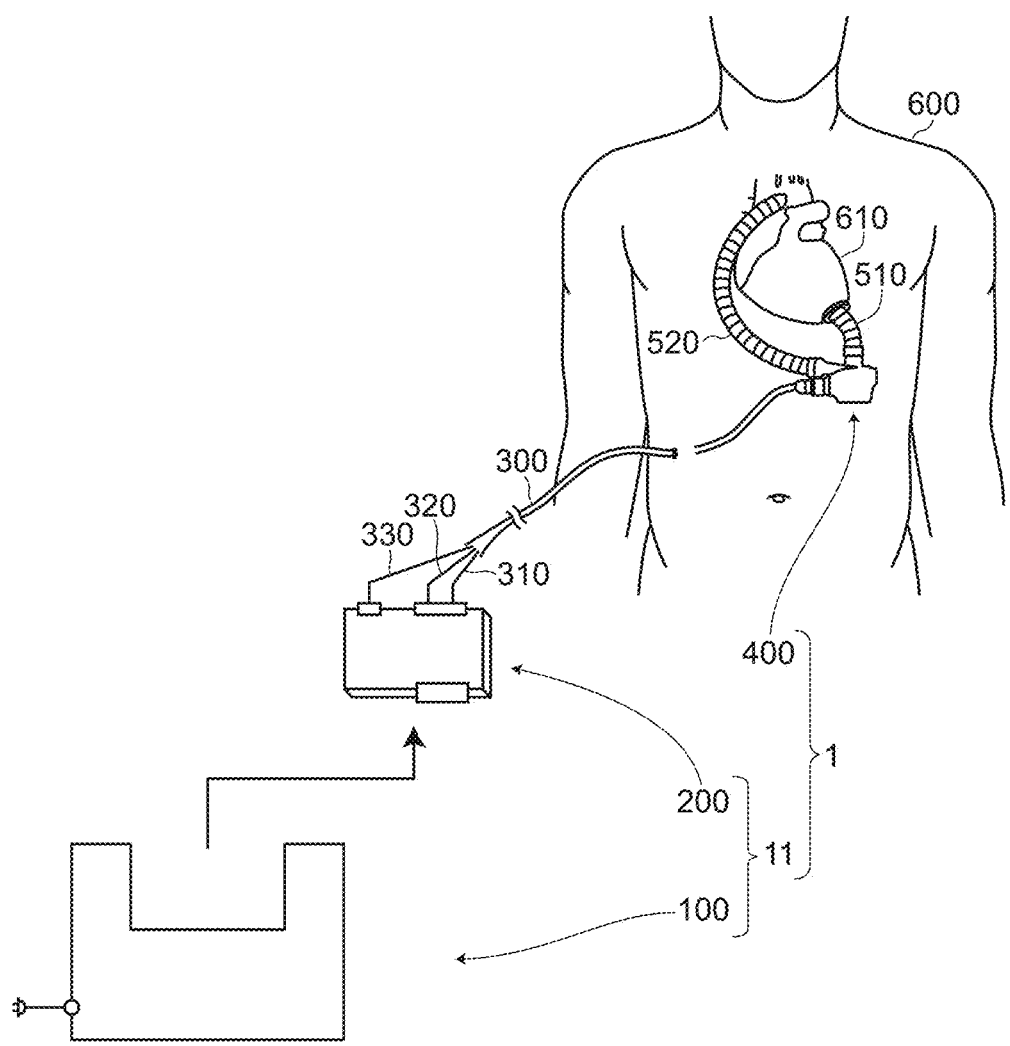
FIG. 1 is a schematic view for describing a ventricular assist system 1 and a blood pump controller 11 according to an embodiment 1.

FIG. 1 is a schematic view for describing the ventricular assist system 1 and the blood pump controller 11 used in the ventricular assist system 1 according to the embodiment 1.

As shown in FIG. 1, the ventricular assist system 1 includes a blood pump 400 embedded in a body of a user 600, an artificial blood vessel 510 which connects the blood pump 400 and a left ventricle (not shown in the drawing) of an actual heart 610 of the user 600; an artificial blood vessel 520 for returning blood from the blood pump 400 to a living body of the user; the blood pump controller 11 disposed outside the body of the user 600, an up tube 310 and a down tube 320 which connect the blood pump controller 11 and the blood pump 400; and an electric cable 330.

The blood pump 400 assists a blood supply function which the actual heart 610 of the user 600 has. The blood pump 400 has a blood supply function of making blood of the user 600 flow into a pump chamber (described later) and flow out from the pump chamber into the inside of the user 600. As the blood pump 400, a so-called centrifugal type blood pump can be adopted.

The blood pump controller 11 drives the blood pump 400, and supplies a cool sealing liquid L1 (described later) to the blood pump 400. The blood pump controller 11 also recovers the cool sealing liquid L1 which is returned to the inside of the blood pump 400 after circulation.

The up tube 310 makes the cool sealing liquid L1 flow from the blood pump controller 11 to the blood pump 400. The down tube 320 makes the cool sealing liquid L1 flow from the blood pump 400 to the blood pump controller 11. As the up tube 310 and the down tube 320, a tube for piping can be used.

A drive signal is transmitted from the blood pump controller 11 to the blood pump 400 through the electric cable 330.

With respect to these three constitutional elements consisting of the up tube 310, the down tube 320, and the electric cable 330, cable processing may be adopted so as to bundle these three constitutional elements into one cable (shown as a pump cable 300 in FIG. 1), cable processing may be adopted so as to bundle two constitutional elements out of these three constitutional elements into one cable, or cable processing may be adopted so as to form three constitutional elements as independent cables respectively.

The blood pump controller 11 is formed of at least a first sub controller 100 (also referred to as "home station") and a second sub controller 200 (also referred to as "portable side controller"). These first sub controller 100 and the second sub controller 200 are separable from each other and joinable with each other using the configuration described later.

In the description made hereinafter, with respect to joining between the first sub controller and the second sub controller, there may be cases where "joining" is replaced with the term "connecting" or the term "docking".

(2) Blood Pump 400 and Cool Sealing Liquid L1

Figure 2A:
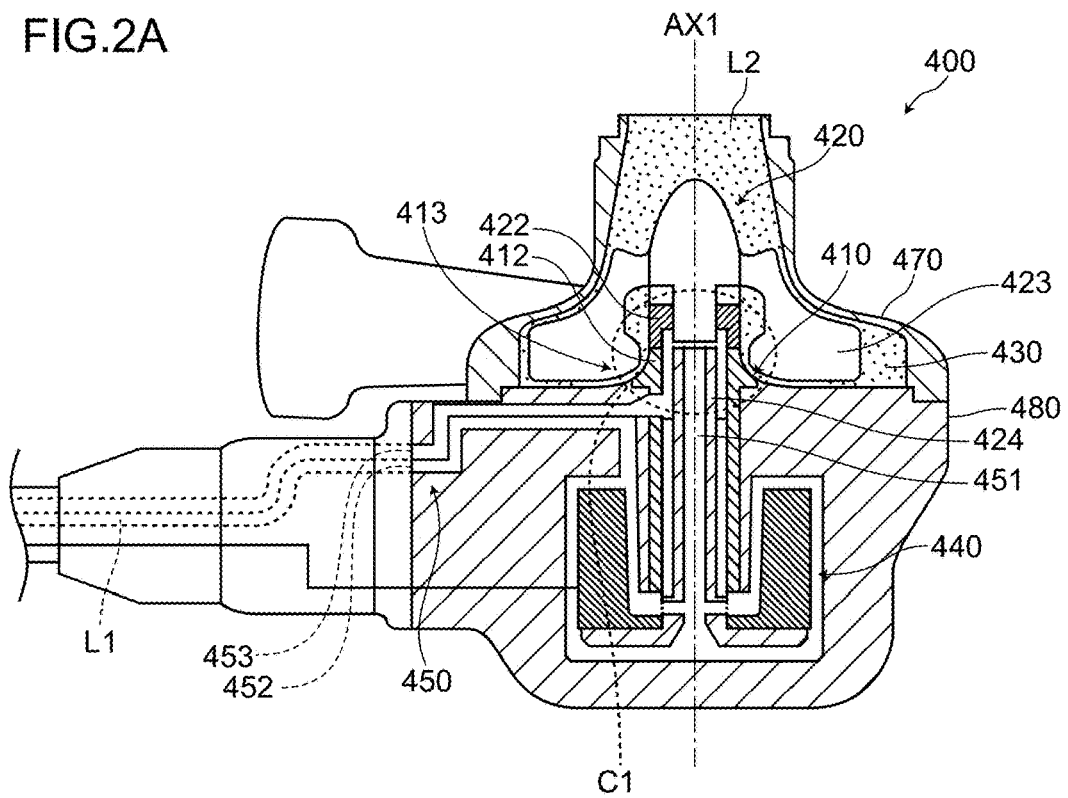
FIG. 2A to FIG. 2C are views for describing a blood pump 400 of the ventricular assist system 1 according to the embodiment 1.
Figure 2B:
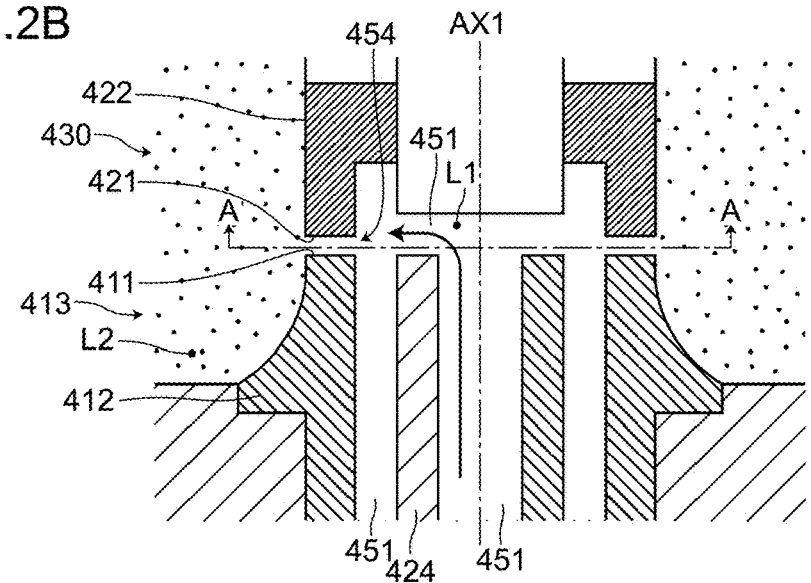
Figure 2C:
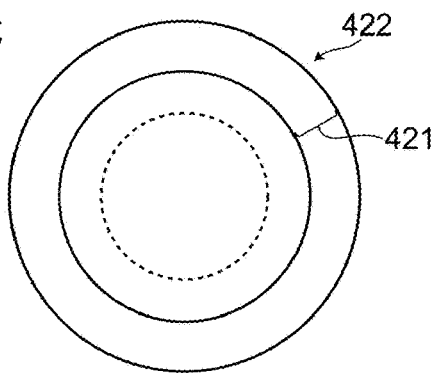

FIG. 2A to FIG. 2C are views for describing the blood pump 400 of the ventricular assist system 1 according to the embodiment 1. FIG. 2A is a cross-sectional view showing the overall structure of the blood pump 400. FIG. 2B is a cross-sectional view of a main part showing a part of the blood pump 400 surrounded by a dotted line C1 shown in FIG. 2A in an enlarged manner. FIG. 2C is a plan view of a rotary side slide member 422 taken along a line A-A in FIG. 2B as viewed along an arrow.

As shown in FIG. 2A and FIG. 2B, the blood pump 400 includes: a fixed side slide member 412 having an annular first slide surface 411; the rotary side slide member 422 having an annular second slide surface 421 (see also FIG. 2C); a blood pump chamber 430 positioned on an outer peripheral side of the fixed side slide member 412 and the rotary side slide member 422; an impeller 423 housed in the blood pump chamber 430 and being integrally rotatable with the rotary side slide member 422; a motor 440 capable of imparting rotary energy to the impeller 423; and a cool sealing liquid flow chamber 451 which is positioned on an inner peripheral side of the fixed side slide member 412 and the rotary side slide member 422 and through which a cool sealing liquid L1 supplied from an outside flows.

A rotary part 420 formed of the impeller 423, the rotary side slide member 422, a shaft 424 (described later) and the like is rotatable about a rotary axis AX1.

The blood pump chamber 430 is formed so as to be surrounded by an upper casing 470 and a lower casing 480 which is fixedly joined to the fixed side slide member 412. The cool sealing liquid flow chamber 451 is formed so as to be surrounded by the shaft 424, a bearing 413 (the fixed side slide member 412 being included in a part of the bearing 413) and the like on an inner peripheral side of the fixed side slide member 412 and the rotary side slide member 422.

The blood pump 400 is used in a state where the first slide surface 411 and the second slide surface 421 are brought into contact with each other, and the cool sealing liquid L1 is supplied to a gap 454 formed between the first slide surface 411 and the second slide surface 421 from the cool sealing liquid flow chamber 451.

The first slide surface 411 of the fixed side slide member 412 and the second slide surface 421 of the rotary side slide member 422 are brought into contact with each other in an opposedly facing manner. When the cool sealing liquid L1 is supplied to such a contact portion, a slight gap 454 is formed on a part of the contact portion or on the whole contact portion, and the cool sealing liquid L1 enters the gap 454.

"Cool sealing liquid L1" flows through between the shaft 424 of the motor 440 for imparting a rotational force to the impeller 423 and a fixed portion 410 such as the fixed side slide member 412 (forming a part of the cool sealing liquid flow chamber), and the cool sealing liquid L1 is used for cooling and lubricating the shaft 424 and the fixed portion 410.

Further, as described previously, the cool sealing liquid L1 is supplied to the gap 454 formed between the first slide surface 411 of the fixed side slide member 412 and the second slide surface 421 of the rotary side slide member 422 as a sealing liquid thus preventing the intrusion of a blood component into the gap 454 formed between the first slide surface 411 and the second slide surface 421.

(3) Blood Pump Controller 11

The blood pump controller 11 is the blood pump controller used in the ventricular assist system 1.

Figure 3A:
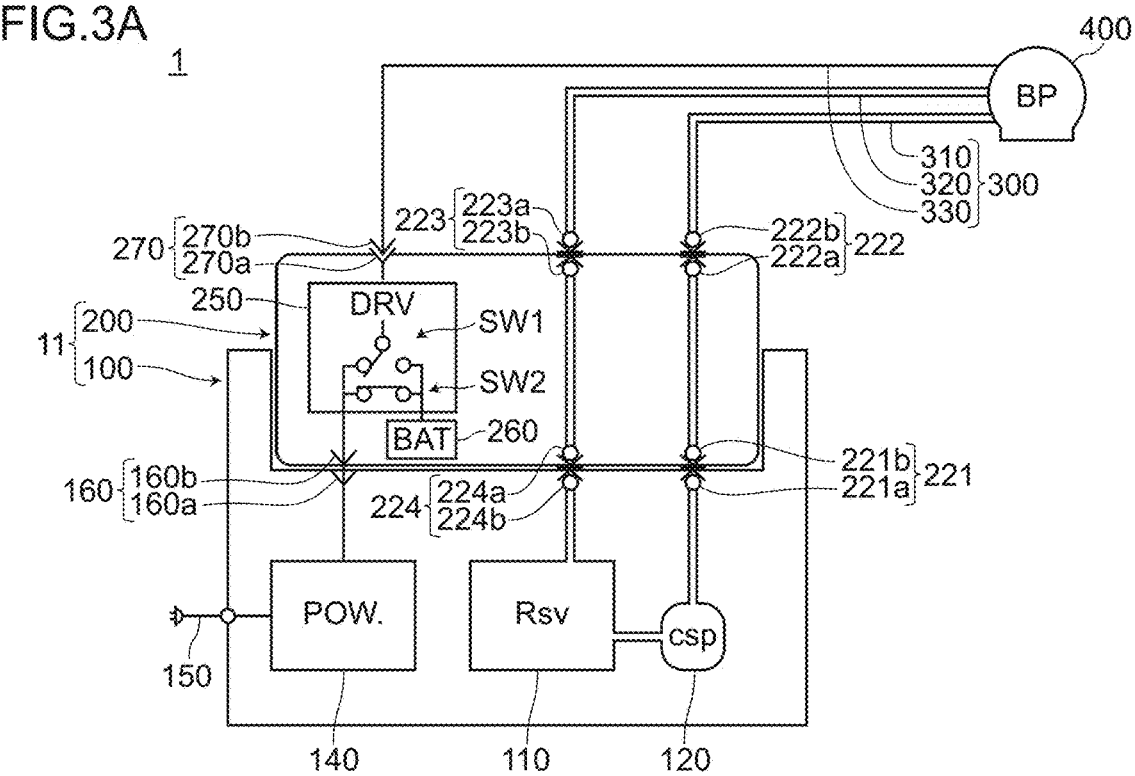
FIG. 3A and FIG. 3B are block diagrams for describing the ventricular assist system 1 and the blood pump controller 11 according to the embodiment 1.
Figure 3B:
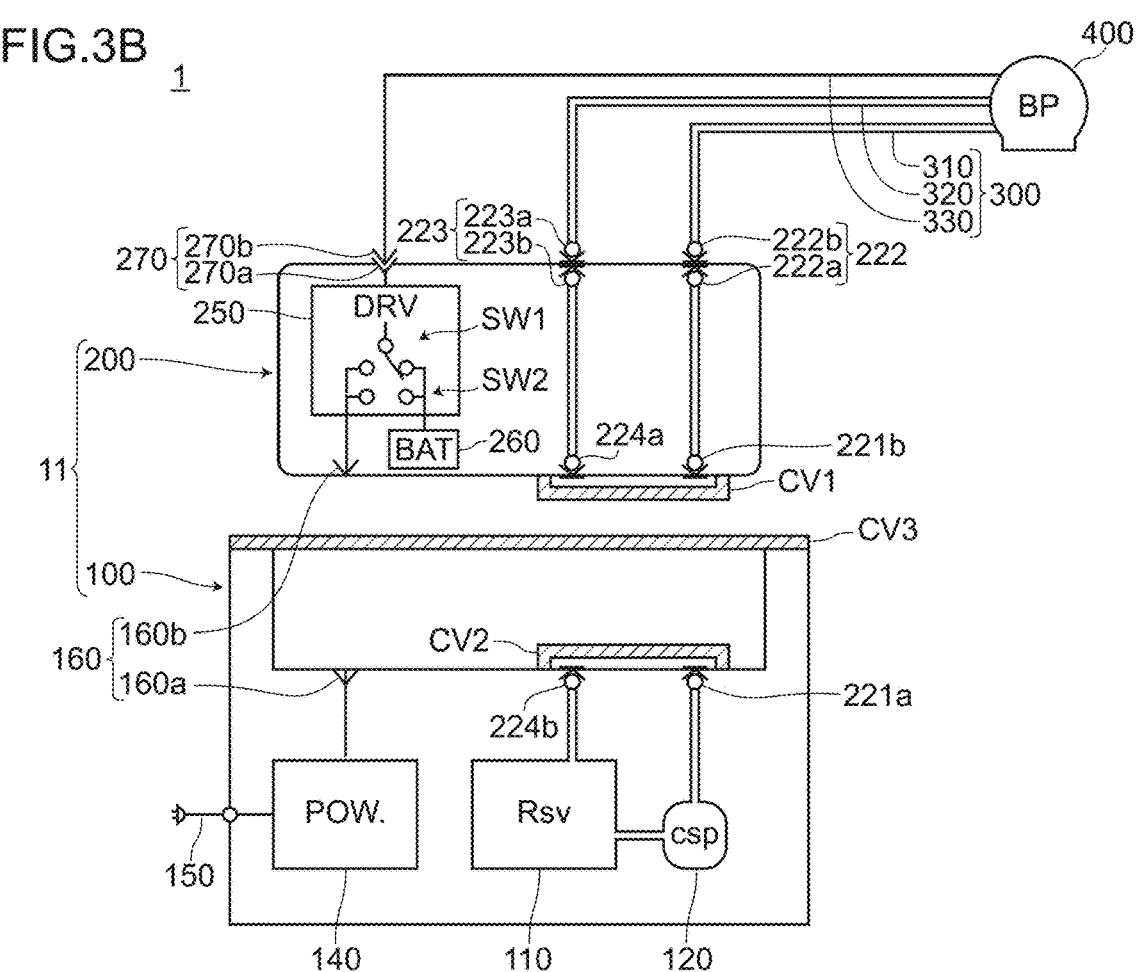

FIG. 3A and FIG. 3B are block diagrams for describing the ventricular assist system 1 and the blood pump controller 11 according to the embodiment 1. FIG. 3A is a block diagram showing a state where the second sub controller 200 is connected to the first sub controller 100 (a docked state). FIG. 3B is a view showing a state where the second sub controller 200 is separated from the first sub controller 100.

As shown in FIG. 3A, the blood pump controller 11 includes at least: a blood pump drive circuit 250, a battery 260, a first cool sealing liquid reservoir 110, a cool sealing liquid pump 120, a first pipe joint 221, a second pipe joint 222, a third pipe joint 223, and a fourth pipe joint 224.

The blood pump drive circuit 250 is electrically connected to the electric cable 330, and drives the motor 440 of the blood pump 400 (see FIG. 2A).

The battery 260 is electrically connected to the blood pump drive circuit 250, and supplies a power source to the blood pump drive circuit 250.

The first cool sealing liquid reservoir 110 reserves the cool sealing liquid L1.

The cool sealing liquid pump 120 sucks the cool sealing liquid L1 supplied from the first cool sealing liquid reservoir 110, and supplies the sucked cool sealing liquid L1. The cool sealing liquid pump 120 can increase a supply pressure of the cool sealing liquid L1 to be supplied toward a blood pump 400 side. As the cool sealing liquid pump 120, a diaphragm pump can be adopted, for example.

The first pipe joint 221 is formed of a first pipe joint upstream side 221a and a first pipe joint downstream side 221b which are detachably connectable with each other. The first pipe joint 221 relays the cool sealing liquid L1 supplied from the cool sealing liquid pump 120.

The second pipe joint 222 is formed of a second pipe joint upstream side 222a and a second pipe joint downstream side 222b which are detachably connectable with each other. The second pipe joint downstream side 222b of the second pipe joint 222 is connected to the up tube 310, and the second pipe joint 222 relays the cool sealing liquid L1 supplied from the first pipe joint 221 to the up tube 310.

The third pipe joint 223 is formed of a third pipe joint upstream side 223a and a third pipe joint downstream side 223b which are detachably connectable with each other. The third pipe joint upstream side 223a of the third pipe joint 223 is connected to the down tube 320, and the third pipe joint 223 relays the cool sealing liquid L1 supplied from the down tube 320 to the inside of the blood pump controller 11.

The fourth pipe joint 224 is formed of a fourth pipe joint upstream side 224a and a fourth pipe joint downstream side 224b which are detachably connectable with each other. The fourth pipe joint 224 relays the cool sealing liquid L1 supplied from the third pipe joint downstream side 223b to the first cool sealing liquid reservoir 110.

In the above-mentioned configuration, "connectable with" means that the constitutional elements are connectable so as to form a cool sealing liquid flow path (a liquid circuit). As members used for connection, pipes, tubes or the like can be adopted.

"pipe joint" may be any part provided that the flow path of the cool sealing liquid L1 can be shut off from each other or connected to each other. For example, a part which is usually referred to as a coupling or a coupler (a registered trademark of NITTO KOHKI CO., LTD.) can be used as the pipe joint in the embodiment 1.

An upstream side of the pipe joint (the first pipe joint upstream side 221a, the second pipe joint upstream side 222a, the third pipe joint upstream side 223a or the fourth pipe joint upstream side 224a) may be of a plug type or a socket type. Reversely, a downstream side of the pipe joint (the first pipe joint downstream side 221b, the second pipe joint downstream side 222b, the third pipe joint downstream side 223b or the fourth pipe joint downstream side 224b) may be also of a plug type or a socket type.

In this embodiment, as the first pipe joint 221 and the fourth pipe joint 224, a two-tandem pipe joint is used where the first pipe joint 221 and the fourth pipe joint 224 are integrally formed with each other. In the same manner, as the second pipe joint 222 and the third pipe joint 223, a two-tandem pipe joint is used where the second pipe joint 222 and the third pipe joint 223 are integrally formed with each other. However, the embodiment 1 is not limited to such configurations, and the first pipe joint 221 and the fourth pipe joint 224 may be provided independently from each other, and the second pipe joint 222 and the third pipe joint 223 may be provided independently from each other.

FIG. 3A and FIG. 3B show the configuration of a mode where, in connecting the second sub controller 200 and the blood pump 400, the second sub controller 200 and the blood pump 400 are connected with each other using the second pipe joint 222, the third pipe joint 223 and the second connector 270. However, the embodiment 1 is not limited to such a configuration.

For example, the configuration of a mode may be adopted where the up tube 310, the down tube 320 and/or the electric cable 330 are directly guided into the inside of the second sub controller 200, and the up tube 310, the down tube 320 and/or the electric cable 330 are fixed to a housing of the second sub controller 200 by so-called "rubber bushings" or the like. Further, the configuration of a mode may be adopted where the up tube 310 or the down tube 320 and the housing of the second sub controller 200 are fixed to each other by welding the up tube 310 or the down tube 320 and the housing of the second sub controller 200 to each other.

In this case, an end portion of the up tube 310 and the rubber bushing or the welded portion are replaced with "second pipe joint 222", an end portion of the down tube 320 and the rubber bushing or the welded portion are replaced with "third pipe joint 223", and an end portion of the electric cable 330 and the rubber bushing are replaced with "second connector 270". It is also assumed that these configurations are equivalent with the corresponding configurations of the ventricular assist system 1 and the blood pump controller 11 according to the embodiment 1.

In an actual use, however, it is preferable that the second pipe joint 222, the third pipe joint 223 and the second connector 270 be actually introduced. This is because it is possible to perform the maintenance of the up tube 310, the down tube 320 and the electric cable 330 (pump cable 300) by temporarily detaching them from the second sub controller 200, and it is also possible to easily and rapidly connect them to a different second sub controller.

(4) First Sub Controller 100 and Second Sub Controller 200

The blood pump controller 11 is formed of: the first sub controller 100 which includes the first cool sealing liquid reservoir 110, the cool sealing liquid pump 120, the first pipe joint upstream side 221a and the fourth pipe joint downstream side 224b; and the second sub controller 200 which includes the blood pump drive circuit 250, the battery 260, the first pipe joint downstream side 221b, the second pipe joint upstream side 222a, the third pipe joint downstream side 223b and the fourth pipe joint upstream side 224a.

The first sub controller 100 and the second sub controller 200 are separable from each other (see FIG. 3B) or are joinable to each other (see FIG. 3A) by detachably connecting the first pipe joint 221 (the first pipe joint upstream side 221a, the first pipe joint downstream side 221b) and the fourth pipe joint 224 (the fourth pipe joint upstream side 224a, the fourth pipe joint downstream side 224b) respectively.

As shown in FIG. 3A and FIG. 3B, the blood pump controller 11 may further include a power source plug 150, a power source circuit 140, a first connector 160 (a first connector/receptacle 160a, a first connector/plug 160b), the second connector 270 (a second connector/receptacle 270a, a second connector/plug 270b) and the like.

(5) Electrical Connection Relationship

The ventricular assist system 1 according to the embodiment 1 has the following electrical connection relationship.

The power source plug 150 is connected to an input stage of the power source circuit 140, an output stage of the power source circuit 140 is connected to an input stage of the blood pump drive circuit 250 mounted on the second sub controller 200 via the first connector 160 (160a, 160b). The battery 260 is connected to another input stage of the blood pump drive circuit 250. An output stage of the blood pump drive circuit 250 is connected to the electric cable 330 via the second connector 270 (270a, 270b), and is eventually connected to the motor 440 and the like in the blood pump 400 (see FIG. 2A).

In the drawings, the indication of symbols for the input stages and the output stages of the respective circuits is omitted.

(6) Relay Port Shut Off Means

In the embodiment 1, the first pipe joint upstream side 221a, the first pipe joint downstream side 221b, the fourth pipe joint upstream side 224a, and the fourth pipe joint downstream side 224b respectively include a relay port shut off means (not shown in the drawing). The relay port shut off means is disposed in the vicinity of a relay port (not shown in the drawing) which appears when a pipe joint of each of said respective sides is separated from a pipe joint of a counterpart side which forms a pair with said each of the sides, and shuts off the outside and the inside of the relay port from each other. In other words, at least the first pipe joint upstream side 221a, the first pipe joint downstream side 221b, the fourth pipe joint upstream side 224a and the fourth pipe joint downstream side 224b are formed of a so-called "self seal type" pipe joint where a flow path of a liquid is automatically sealed when a pipe joint of each of said respective sides is separated from a pipe joint of a counterpart side which forms a pair with said each of the sides.

"a pipe joint of a counterpart side which forms a pair with said each of the sides" indicates the first pipe joint downstream side 221b in case of the first pipe joint upstream side 221a, indicates the first pipe joint upstream side 221a in case of the first pipe joint downstream side 221b, indicates the fourth pipe joint downstream side 224b in case of the fourth pipe joint upstream side 224a, and indicates the fourth pipe joint upstream side 224a in case of the fourth pipe joint downstream side 224b.

"relay port shut off means" may be any means provided that the means can shut off the outside and the inside of the relay port from each other when a pipe joint of each of said respective sides is separated from a pipe joint of a counterpart side which forms a pair with said each of the sides, and the means can make the inside and the outside of the relay port communicate with each other when a pipe joint of each of said respective sides is connected to a pipe joint of a counterpart side which forms a pair with said each of the sides. The relay port shut off means may be formed of a check valve, for example.

It is preferable that the second pipe joint upstream side 222a, the second pipe joint downstream side 222b, the third pipe joint upstream side 223a and the third pipe joint downstream side 223b also respectively have a relay port shut off means (not shown in the drawing) in the same manner.

2. Connection and Separation of Blood Pump Controller 11 According to Embodiment 1

(1) Case where Second Sub Controller 200 is Connected to First Sub Controller 100

In the case where a user (patient) stays within a fixed range in a mode where frequency of movement is low and a moving distance is short (in the case where the user stays at home, an office or the like, for example), the user uses the blood pump controller 11 in a state where the second sub controller 200 is connected (docked) to the first sub controller 100.

In this case, the blood pump controller 11 is operated in a state where the first sub controller 100 and the second sub controller 200 are integrally formed with each other. Hereinafter, the summary of the operation in this case is described with reference to FIG. 3A.

a) Electric Flow and Operation

An external power source (AC 100 V, for example) which is taken into from the power source plug 150 is supplied to the power source circuit 140. In the power source circuit 140, an internal power source (DC 18 V or the like, for example) necessary for operating the blood pump controller 11 is generated based on the external power source. The internal power source which the power source circuit 140 generates is supplied from the inside of the first sub controller 100 to the second sub controller 200 via the first connector 160 (160*a*, 160*b*). In the second sub controller 200, the internal power source supplied via the first connector 160 is supplied to the blood pump drive circuit 250. Along with such an operation, a predetermined internal power source is supplied to the cool sealing liquid pump 120.

The blood pump drive circuit 250 generates a motor drive signal for driving the motor 440 in the blood pump 400. The motor drive signal is relayed by the second connector 270 (270*a*, 270*b*) and is eventually transmitted to the motor 440 in the blood pump 400 via the electric cable 330. As a result, the motor 440 in the blood pump 400 is driven so that the impeller 423 is rotated.

In this embodiment 1, the configuration is adopted where, as an internal power source for operating the blood pump drive circuit 250, an internal power source generated by the power source circuit 140 is used by connecting a first switch SW1 in the blood pump drive circuit 250 to a first connector 160 side. However, the embodiment 1 is not limited to such a configuration. For example, the configuration may be adopted where the whole internal power source necessary for the blood pump drive circuit 250 is generated in the second sub controller 200. Further, for example, the configuration may be adopted where an internal power source generated by the battery 260 (battery 260 being a battery to which electric energy is charged suitably when necessary) is used as an internal power source for operating the blood pump drive circuit 250 by connecting the first switch SW1 to a battery 260 side and by bringing a second switch SW2 into a released state.

b) Circulation of Cool Sealing Liquid L1

The cool sealing liquid L1 is stored in the first cool sealing liquid reservoir 110. The cool sealing liquid L1 supplied from the first cool sealing liquid reservoir 110 flows into the cool sealing liquid pump 120. The cool sealing liquid L1 is sucked into the cool sealing liquid pump 120 by a pump mechanism (for example, a pump mechanism of a diaphragm pump or the like) of the cool sealing liquid pump 120, and a pressure of the cool sealing liquid L1 is increased and the cool sealing liquid L1 is supplied toward the first pipe joint 221.

The first pipe joint upstream side 221*a* and the first pipe joint downstream side 221*b* are connected to each other, and a first sub controller 100 side and a second sub controller 200 side communicate with each other in the vicinity of the respective relay ports of the first pipe joint upstream side 221*a* and the first pipe joint downstream side 221*b* respectively. With such a configuration, using the first pipe joint 221 (the first pipe joint upstream side 221*a*, the first pipe joint downstream side 221*b*) as a boundary, the cool sealing liquid L1 strides over the boundary, and the cool sealing liquid L1 is transferred from the first sub controller 100 to the second sub controller 200. In the same manner, using the second pipe joint 222 (the second pipe joint upstream side 222*a*, the second pipe joint downstream side 222*b*) as a boundary, the cool sealing liquid L1 strides over the boundary, and the cool sealing liquid L1 is transferred from the second sub controller 200 to the up tube 310.

Then, the cool sealing liquid L1 flows through the up tube 310, and is guided into the blood pump 400 from a pump inflow port 452 for the cool sealing liquid (see FIG. 2A). The cool sealing liquid L1 is supplied to the gap 454 formed between the first slide surface 411 of the fixed side slide member 412 and the second slide surface 421 of the rotary side slide member 422 via the cool sealing liquid flow chamber 451.

The remaining cool sealing liquid L1 which does not enter the gap 454 formed between the first slide surface 411 and the second slide surface 421 is returned to the flow path in the down direction. That is, the cool sealing liquid L1 is returned to the second sub controller 200 via a pump flowout port 453 for the cool sealing liquid, the down tube 320 and the third pipe joint 223 (the third pipe joint upstream side 223*a*, the third pipe joint downstream side 223*b*). Then, using the fourth pipe joint 224 (the fourth pipe joint upstream side 224*a*, the fourth pipe joint downstream side 224*b*) as a boundary, the cool sealing liquid L1 strides over the boundary and the cool sealing liquid L1 is transferred from the second sub controller 200 to the first sub controller 100. Then, eventually, the cool sealing liquid L1 is returned from the fourth pipe joint downstream side 224*b* to the first cool sealing liquid reservoir 110.

(2) Separation of Second Sub Controller 200 from First Sub Controller 100

For example, in the case where a user or the like intends to carry only the second sub controller 200 when the user or the like goes out, the user or the like performs an operation of separating the second sub controller 200 from the first sub controller 100.

To be more specific, the second sub controller 200 can be separated from the first sub controller by performing operations such as separating the first pipe joint downstream side 221*b* from the first pipe joint upstream side 221*a*, separating the fourth pipe joint upstream side 224*a* from the fourth pipe joint downstream side 224*b*, or separating the first connector/plug 160*b* from the first connector/receptacle 160*a* when the configuration is adopted where an internal power source used in the second sub controller 200 is received by the first sub controller 100 via the first connector 160.

In an actual operation, it is unnecessary for a user or the like to be conscious of the above-mentioned individual separations of the pipe joints and the connectors. For example, it is preferable that the configuration be adopted where the separation of the individual pipe joints and connectors is automatically performed by performing an operation such as pulling up the second sub controller 200 together with the housing in a state where the first sub controller 100 is fixed.

(3) In the Case where Second Sub Controller 200 is Separated From First Sub Controller 100

In the case where a user (patient) goes out, for example, the blood pump 400 is operated using only the second sub controller 200 which is in a separated state from the first sub controller 100.

Hereinafter, the summary of an operation of the blood pump controller 11 (the second sub controller 200 and the first sub controller 100) in such a case is described with reference to FIG. 3B.

a) Electrical Flow and Operation

When the second sub controller 200 is separated from the first sub controller 100, the blood pump drive circuit 250 in the second sub controller 200 is operated using a power source from the battery 260. For example, the configuration may be adopted where when the second sub controller 200 is separated from the first sub controller 100, the first switch SW1 in the blood pump drive circuit 250 is connected to a battery 260 side so as to fetch an internal power source for operating the inside of the blood pump drive circuit 250 from the battery 260.

The blood pump drive circuit 250 in the second sub controller 200 is operated in the same manner as the operation described in 2. (1) a) so as to rotate the impeller 423.

b) Supply of Cool Sealing Liquid L1

A path through which the cool sealing liquid L1 flows (a flow path forming a part of the cool sealing liquid flow path, for example, a flow path defined by the up tube, the shaft connected to the motor and the bearing, the cool sealing liquid flow chamber or the like) is disposed between the first slide surface 411 and the second slide surface 421 on one side and the second sub controller 200 on the other side. The cool sealing liquid L1 stays in the path through which the cool sealing liquid L1 flows and in the second sub controller 200.

Even if the cool sealing liquid L1 is consumed in the gap 454 formed between the first slide surface 411 and the second slide surface 421, the cool sealing liquid L1 which stays in the path and in the second sub controller 200 sequentially moves to the gap 454 formed between the first slide surface 411 and the second slide surface 421 such that the cool sealing liquid L1 is sucked into the gap 454 formed between the first slide surface 411 and the second slide surface 421. In this manner, it is possible to supply the cool sealing liquid L1 to the gap 454 formed between the first slide surface 411 and the second slide surface 421.

c) Processing at Relay Port of Pipe Joint of Second Sub Controller 200

In the embodiment 1, the first pipe joint 221 and the fourth pipe joint 224 respectively adopt a so-called "self seal type" pipe joint having a relay port shut off means.

Accordingly, at the time of separating the second sub controller 200 from the first sub controller 100, when the first pipe joint downstream side 221b is separated from the first pipe joint upstream side 221a, the flow path for the liquid is automatically sealed by the relay port shut off means on the first pipe joint downstream side 221b. In the same manner, when the fourth pipe joint upstream side 224a is separated from the fourth pipe joint downstream side 224b, the flow path for the liquid is automatically sealed by the relay port shut off means on the fourth pipe joint upstream side 224a.

Further, in an interlocking manner with the separation of the second sub controller 200 from the first sub controller 100, in the vicinity of the relay ports on the first pipe joint downstream side 221b and the fourth pipe joint upstream side 224a, a cover CV1 which covers the respective relay ports is provided (see FIG. 3B).

d) Processing on First Sub Controller 100 Side

When the second sub controller 200 is separated from the first sub controller 100, in the first sub controller 100, an operation of the cool sealing liquid pump 120 is stopped.

Further, the flow path for the liquid is automatically sealed by the relay port shut off means on the first pipe joint upstream side 221a and on the fourth pipe joint downstream side 224b respectively.

In the vicinity of the relay ports on the first pipe joint upstream side 221a and the fourth pipe joint downstream side 224b, a cover CV2 which covers the respective relay ports is provided (see FIG. 3B).

Further, in the vicinity of an opening into which the second sub controller 200 is inserted, a cover CV3 which covers the opening may be provided (see FIG. 3B).

3. Advantageous Effect Obtained by Ventricular Assist System 1 and Blood Pump Controller 11 According to Embodiment 1

(1) In the ventricular assist system 1 and the blood pump controller 11 according to the embodiment 1, the blood pump controller 11 is formed of: the first sub controller 100 which includes the first cool sealing liquid reservoir 110, the cool sealing liquid pump 120, the first pipe joint upstream side 221a, and the fourth pipe joint downstream side 224b; and the second sub controller 200 which includes the blood pump drive circuit 250, the battery 260, the first pipe joint downstream side 221b, the second pipe joint upstream side 222a, the third pipe joint downstream side 223b, and the fourth pipe joint upstream side 224a. The first sub controller 100 and the second sub controller 200 are configured to be separable from each other and joinable to each other by detachably connecting the first pipe joint 221 (221a, 221b) and the fourth pipe joint 224 (224a, 224b).

Due to such a configuration, a user can separate the second sub controller 200 from the first sub controller 100, and can carry only the second sub controller 200. That is, the user can continue an operation of the blood pump 400 by carrying only the second sub controller 200 without carrying the first sub controller 100 which includes the first cool sealing liquid reservoir 110 and the like which have relatively large weight and volume.

For reference, the path through which the cool sealing liquid L1 flows (a flow path forming a part of the cool sealing liquid flow path, for example, a flow path defined by the up tube 310, the shaft 424 connected to the motor and the bearing 413, the cool sealing liquid flow chamber 451 or the like) is disposed between the first slide surface 411 and the second slide surface 421 where the cool sealing liquid L1 is consumed and the second sub controller 200. The cool sealing liquid L1 stays in the path through which the cool sealing liquid L1 flows and in the second sub controller 200. The cool sealing liquid L1 which stays in the path and in the second sub controller 200 is supplied to the gap 454 formed between the first slide surface 411 and the second slide surface 421 (a first liquid replenishing mode). Accordingly, even when only the second sub controller 200 is operated, an operation of the blood pump can be continued while supplying the cool sealing liquid L1 to the gap 454 formed between the first slide surface 411 and the second slide surface 421 over a considerable period.

Accordingly, the present invention can provide the ventricular assist system 1 and the blood pump controller 11 which impose a small burden on a user and has high portability.

(2) In the ventricular assist system 1 and the blood pump controller 11 according to the embodiment 1, the first pipe joint upstream side 221a, the first pipe joint downstream side 221b, the fourth pipe joint upstream side 224a, and the fourth pipe joint downstream side 224b respectively have the relay port shut off means.

With such a configuration, when a user connects the second sub controller 200 to the first sub controller 100 or removes the second sub controller 200 from the first sub controller 100 or when the user carries the second sub controller 200, the outside and the inside (the inside of the first sub controller 100 or the second sub controller 200) in the vicinity of the relay ports are shut off from each other by the relay port shut off means and hence, it is possible to prevent the intrusion of foreign substances, germs or the like from the relay ports to the inside. Further, it is also possible to prevent a leakage of a cool sealing liquid from the inside. In this manner, an operation of the blood pump 400 can be continued safely and hygienically even after the second sub controller 200 is separated.

(3) In an interlocking manner with the separation of the second sub controller 200 from the first sub controller 100, in the vicinity of the relay ports on the first pipe joint downstream side 221b and the fourth pipe joint upstream side 224a, the cover CV1 which covers the respective relay ports is provided.

With such a configuration, the relay ports of the first pipe joint downstream side 221b and the fourth pipe joint upstream side 224a are covered by the cover CV1 and hence, it is possible to protect the first pipe joint downstream side 221b and the fourth pipe joint upstream side 224a. That is, the deformation of the first pipe joint downstream side 221b and the fourth pipe joint upstream side 224a can be prevented. The intrusion of foreign substances, germs or the like into the first pipe joint downstream side 221b and the fourth pipe joint upstream side 224a from an external field can be prevented. It is possible to prevent a hand of a human from touching the first pipe joint downstream side 221b and the fourth pipe joint upstream side 224a.

Substantially the same advantageous effects can be also obtained by the cover CV2 and the cover CV3.

Embodiment 2

Next, a ventricular assist system 2 (to be more specific, a blood pump 400a) according to the embodiment 2 is described with reference to FIG. 4A to FIG. 5. The description of constitutional elements of the embodiment 2 which are substantially equal to the corresponding constitutional elements of the embodiment 1 is omitted.

Figure 4A:
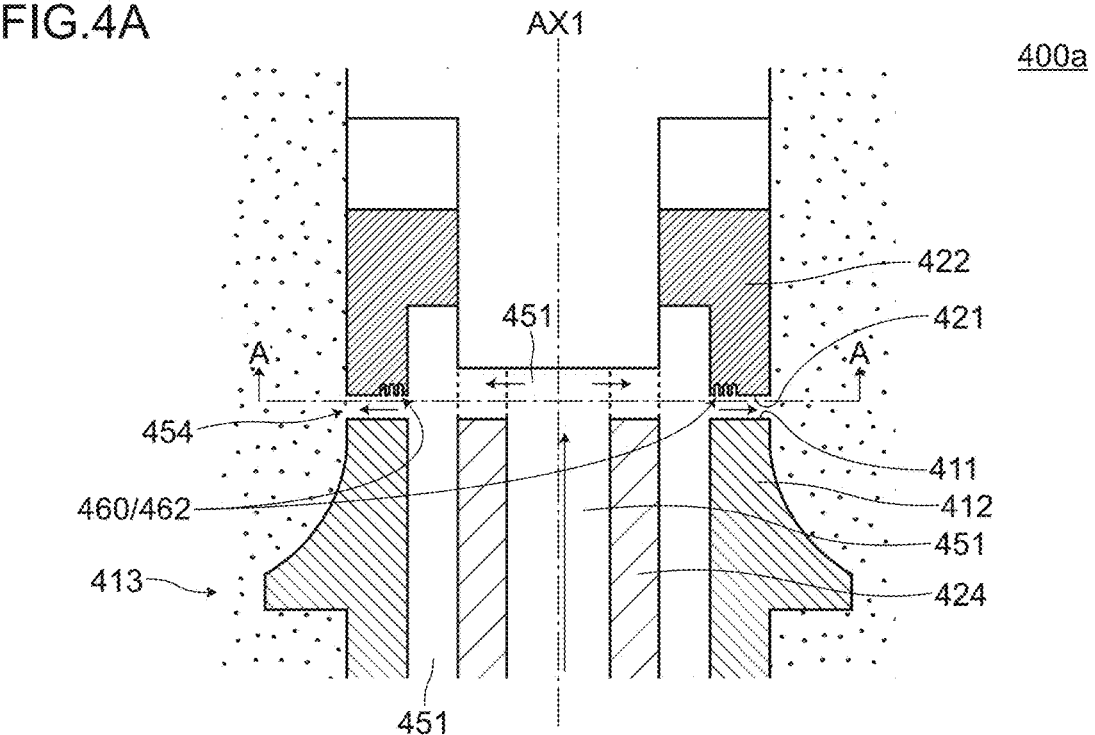
FIG. 4A to FIG. 4D are views for describing a blood pump 400a according to an embodiment 2.
Figure 4B:
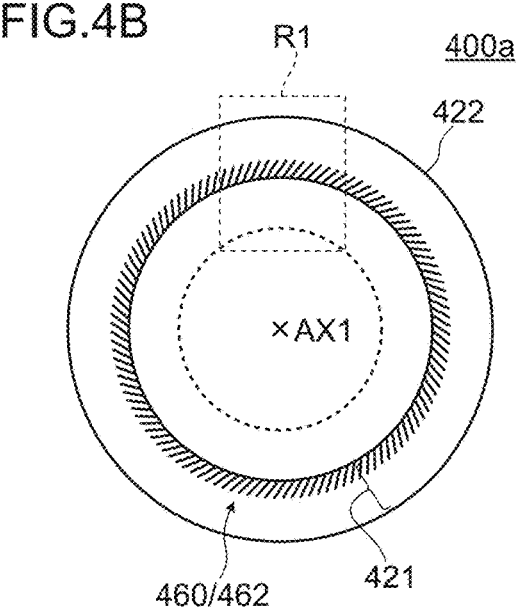
Figure 4C:
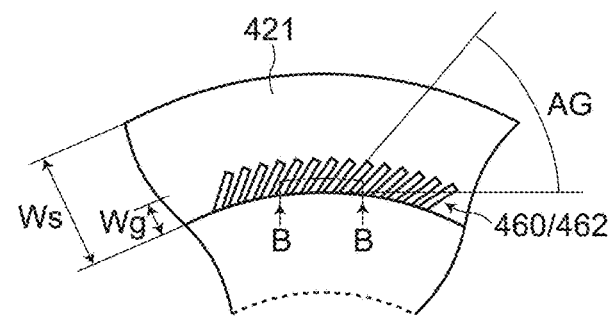
Figure 4D:
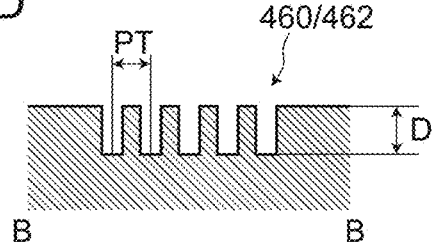

FIG. 4A to FIG. 4D are views for describing the blood pump 400a according to the embodiment 2. FIG. 4A is a cross-sectional view of a main part showing a part of the blood pump 400a corresponding to the part surrounded by a dotted line C1 shown in FIG. 2A in an enlarged manner. FIG. 4B is a plan view of a rotary side slide member 422 taken along a line A-A in FIG. 4A as viewed in an arrow direction. FIG. 4C is an enlarged view showing a portion surrounded by a dotted line R1 in FIG. 4B in an enlarged manner. FIG. 4D is a cross-sectional view of dynamic pressure grooves 460/462 taken along a line B-B in FIG. 4C as viewed in an arrow direction.

Figure 5:
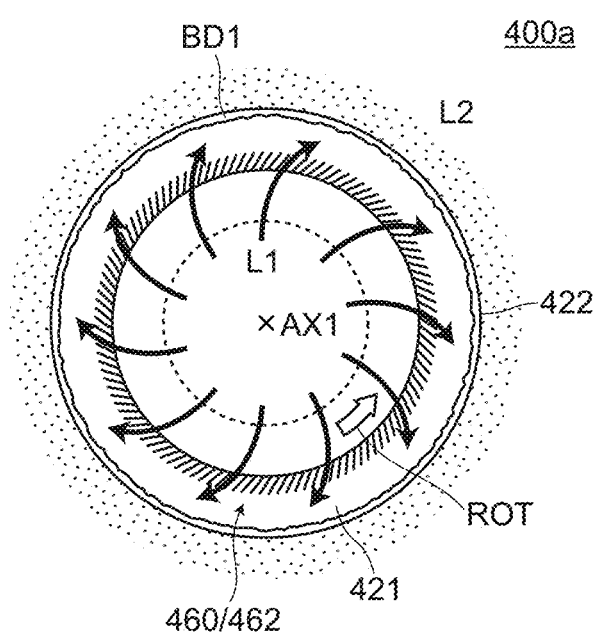
FIG. 5 is a view for describing the movement of a cool sealing liquid L1 when the blood pump 400a according to the embodiment 2 is used.

FIG. 5 is a view for describing the movement of a cool sealing liquid L1 when the blood pump 400a according to the embodiment 2 is used. FIG. 5 is a plan view of the rotary side slide member 422 taken along a line A-A in FIG. 4A as viewed in an arrow direction. The direction of an arrow indicated by ROT indicates a rotational direction of the rotary side slide member 422. An Arrow attached in association with L1 is an arrow for describing the flow of the cool sealing liquid L1 in an exemplifying manner and for the convenience sake. A line indicated by BD1 indicates a boundary between the cool sealing liquid L1 and blood L2.

In this embodiment, BD1 is a line which indicates one example where the boundary between the cool sealing liquid L1 and the blood L2 is in a relatively favorable state.

The ventricular assist system 2 according to the embodiment 2 has basically substantially the same configuration as the ventricular assist system 1 according to the embodiment 1. However, the ventricular assist system 2 according to the embodiment 2 differs from the ventricular assist system 1 according to the embodiment 1 with respect to the configuration of a cool sealing liquid flow path.

(1) Dynamic Pressure Grooves 460

That is, in the blood pump 400a of the ventricular assist system 2 according to the embodiment 2, the dynamic pressure grooves 460 are formed on a member which forms a part of the cool sealing liquid flow path (see FIG. 4A).

In this embodiment, "cool sealing liquid flow path" is a collective term of a path through which the cool sealing liquid L1 may flow in a first sub controller 100, a second sub controller 200, an up tube 310, the blood pump 400/400a, and a down tube 320. "the cool sealing liquid flow path (part) in the blood pump 400a" means the entire path through which the cool sealing liquid flows from a pump inflow port 452 to a pump flowout port 453. "the cool sealing liquid flow path (part) in the blood pump 400a" also includes a cool sealing liquid flow chamber 451, a flow path defined by a shaft 424 connected to a motor 440 and a bearing 413, a gap 454 formed between a first slide surface 411 of a fixed side slide member 412 and a second slide surface 421 of the rotary side slide member 422 and the like.

"dynamic pressure grooves 460" mean grooves in general which can generate a dynamic pressure effect in the flow of the cool sealing liquid L1.

The ventricular assist system 2 (to be more specific, the blood pump 400a) according to the embodiment 2 has such a configuration and hence, fluidity of the cool sealing liquid L1 is accelerated by the dynamic pressure grooves 460 and hence, the cool sealing liquid L1 can be more effectively guided to the gap 454 formed between the first slide surface 411 and the second slide surface 421. Accordingly, the dynamic pressure grooves 460 can compensate for a function which the cool sealing liquid pump 952 performs in the conventional ventricular assist system.

(2) Dynamic Pressure Grooves which are Grooves Formed on First Slide Surface 411 or Second Slide Surface 421

It is preferable that the dynamic pressure grooves 460 be formed of grooves formed on the first slide surface 411 of the fixed side slide member 412 or the second slide surface 421 of the rotary side slide member 422.

For example, the dynamic pressure grooves 462 may be formed on the second slide surface 421 of the rotary side slide member 422 (see FIG. 4A and FIG. 4B). To be more specific, as shown in FIG. 4B, the dynamic pressure grooves 462 may be formed by disposing grooves having an angle with respect to a tangent of an inner periphery set to an angle AG and having a depth in a direction perpendicular to the second slide surface 421 set to a depth D at a pitch PT along an inner peripheral side of the rotary side slide member 422 having the annular second slide surface 421.

In such a configuration, for example, in the case where injection-use water is used as the cool sealing liquid L1, an outer diameter of the second slide surface 421 of the rotary side slide member 422 falls within a range of approximately 7 to 15 mm, a width Ws of the second slide surface 421 in a radial direction falls within a range of approximately 1.0 mm to 2.0 mm, the angle AG falls within a range of 25° to 65° (preferably, 40° to 50°), the depth D falls within a range of 100 nm to 200 nm (preferably, 130 to 170 nm), and the pitch PT falls within a range of 300 nm to 700 nm (preferably, 400 nm to 600 nm), and a width Wg of the dynamic pressure groove in a radial direction falls within a range of 0.3 mm to 0.7 mm (see FIG. 4C and FIG. 4D).

When the rotary side slide member 422 is rotated in a direction of an arrow indicated by ROT (see FIG. 5), the first slide surface 411 of the fixed side slide member 412 which forms a counterpart in sliding and the second slide surface 421 of the rotary side slide member 422 rotate relative to each other.

Out of the first slide surface 411 and the second slide surface 421 which rotate relative to each other, by forming the dynamic pressure grooves 460/462 on at least one of the first slide surface 411 and the second slide surface 421 (the second slide surface 421 in FIG. 4A to FIG. 5), a dynamic pressure effect is imparted to the cool sealing liquid L1 filled in the gap 454 formed between the first slide surface 411 and the second slide surface 421 and hence, a drawing effect applied to the cool sealing liquid L1 filled in the gap 454 formed between the first slide surface 411 and the second slide surface 421 can be increased (see FIG. 5). As a result, it is possible to more effectively guide the cool sealing liquid L1 to the gap 454 formed between the first slide surface 411 and the second slide surface 421.

Eventually, a state of the cool sealing liquid L1 in the gap 454 formed between the first slide surface 411 and the second slide surface 421 can be brought into a state closer to a preferable state and hence, the blood pump can be operated safely and with certainty.

In this embodiment, "a preferred state of the cool sealing liquid L1 in the gap 454 formed between the first slide surface 411 and the second slide surface 421" means a state where a pressure of the cool sealing liquid directed from an inner peripheral side (cool sealing liquid flow chamber side) to an outer peripheral side (blood pump chamber side) of the first slide surface 411 and the second slide surface 421 is relatively high so that a boundary BD1 between the cool sealing liquid L1 and the blood L2 is positioned as close as possible to the outer peripheral side (blood pump chamber side) (see the configuration shown in FIG. 5 as one example).

(3) The shape, the size, the angle and the like of the dynamic pressure groove 460 are not limited to those described above and shown in FIG. 4A to FIG. 5.

The ventricular assist system 2 according to the embodiment 2 has substantially the same configuration as the ventricular assist system 1 according to the embodiment 1 except for the configuration of the cool sealing liquid flow path. Accordingly, the ventricular assist system 2 according to the embodiment 2 acquires the corresponding advantageous effects found amongst all advantageous effects which the ventricular assist system 1 according to the embodiment 1 acquires.

Embodiment 3

Next, a ventricular assist system 3 and a blood pump controller 13 according to the embodiment 3 are described with reference to FIG. 6A and FIG. 6B. The description of constitutional elements of the embodiment 3 which are substantially equal to the corresponding constitutional elements of the embodiments 1 and 2 is omitted.

Figure 6A:
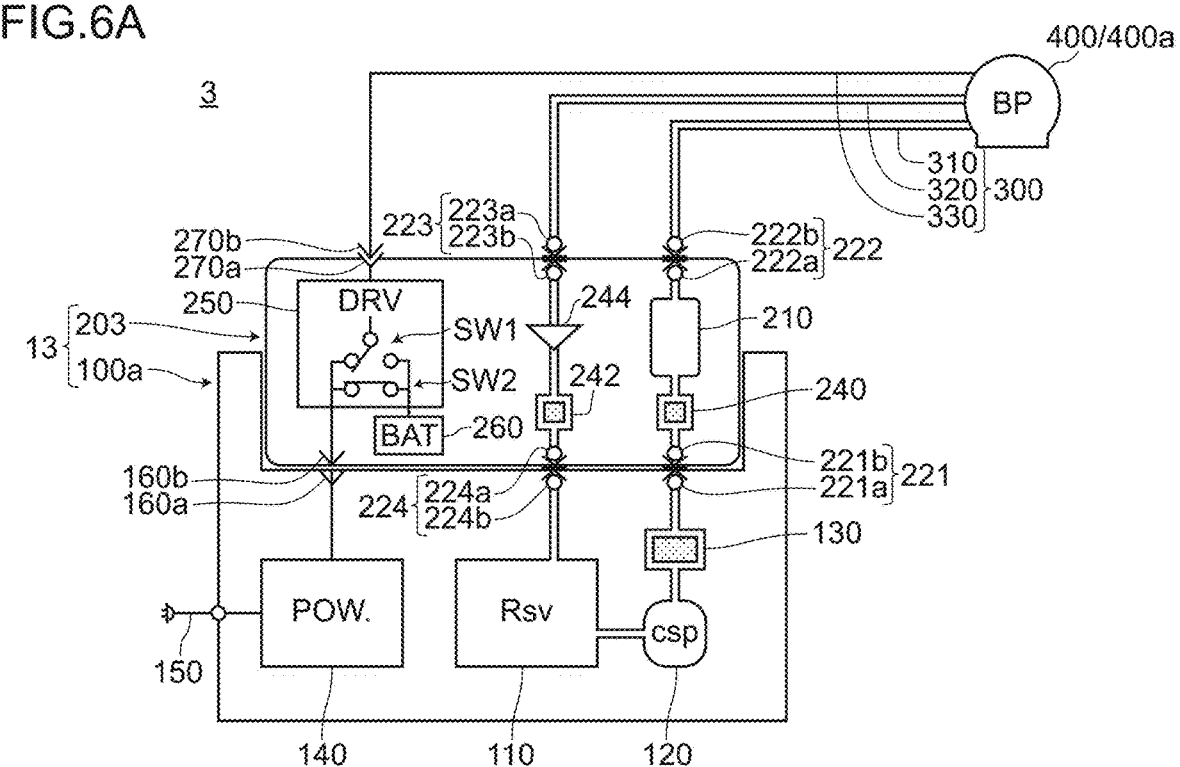
FIG. 6A and FIG. 6B are block diagrams for describing a ventricular assist system 3 and a blood pump controller 13 according to an embodiment 3.
Figure 6B:
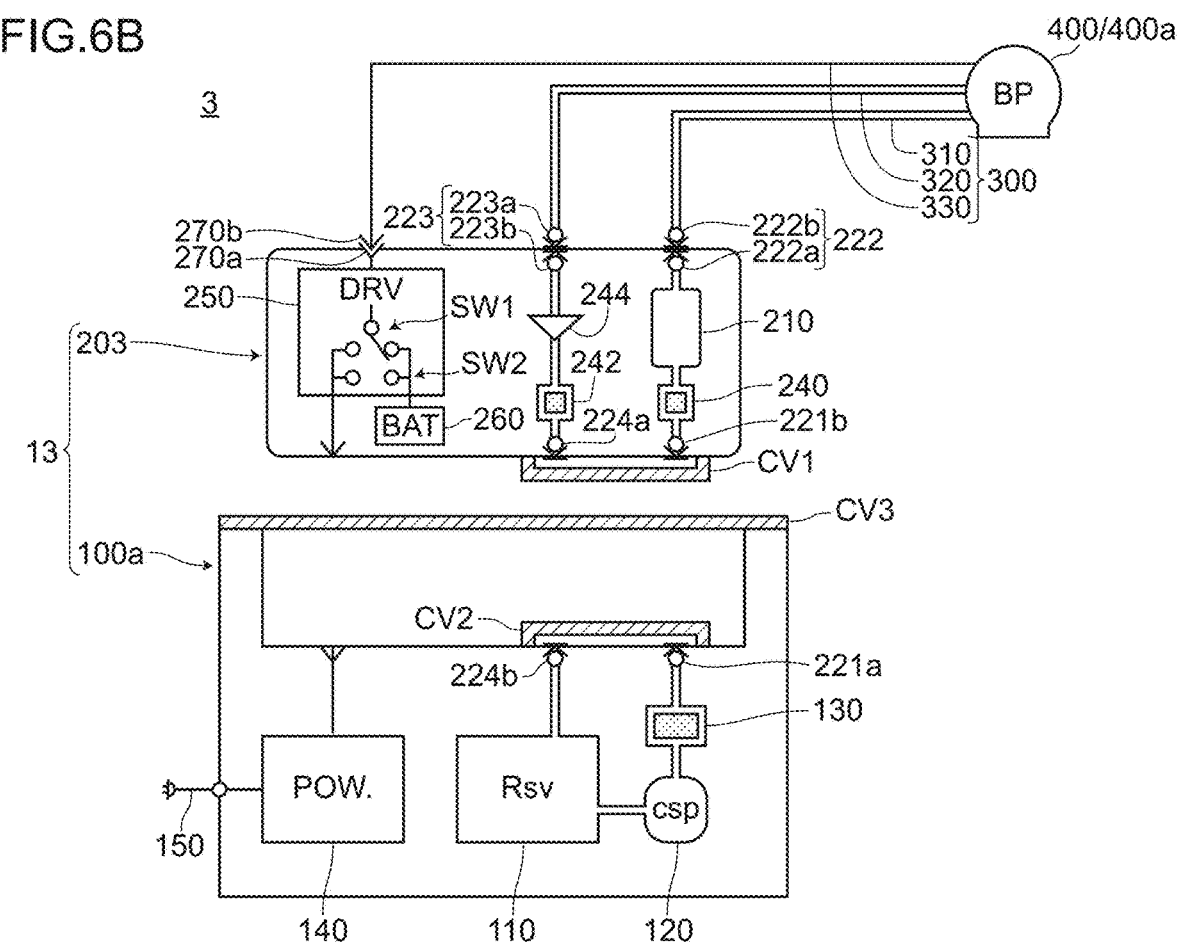

FIG. 6A and FIG. 6B are block diagrams for describing the ventricular assist system 3 and the blood pump controller 13 according to the embodiment 3. FIG. 6A is a block diagram showing a state where a second sub controller 203 is connected to a first sub controller 100a (a docked state).

FIG. 6B is a view showing a state where the second sub controller 203 is separated from the first sub controller 100a.

The ventricular assist system 3 and the blood pump controller 13 according to the embodiment 3 have basically substantially the same configuration as the ventricular assist system 1 and the blood pump controller 11 according to the embodiment 1 and the ventricular assist system 2 according to the embodiment 2. However, the ventricular assist system 3 and the blood pump controller 13 according to the embodiment 3 differ from the ventricular assist system 1 and the blood pump controller 11 according to the embodiment 1 and the ventricular assist system 2 according to the embodiment 2 with respect to the configuration of the blood pump controller.

(1) Second Cool Sealing Liquid Reservoir 210

That is, in the ventricular assist system 3 and the blood pump controller 13 according to the embodiment 3, as shown in FIG. 6A and FIG. 6B, the second sub controller 203 further includes a second cool sealing liquid reservoir 210 which is disposed between a first pipe joint downstream side 221b and a second pipe joint upstream side 222a, has capacity smaller than capacity of a first cool sealing liquid reservoir 110, and stores a cool sealing liquid L1.

The second cool sealing liquid reservoir 210 stores the cool sealing liquid L1, and suitably supplies the cool sealing liquid L1 toward a blood pump 400/400a through an up tube 310.

When the second sub controller 203 is connected to the first sub controller 100a, liquid supply ability of a cool sealing liquid pump 120 also assists so that the cool sealing liquid L1 is supplied to the blood pump 400/400a in the form that the cool sealing liquid L1 stored in the first cool sealing liquid reservoir 110 is mainly replenished, and the second cool sealing liquid reservoir 210 is refilled with the cool sealing liquid L1.

On the other hand, when the second sub controller 203 is separated from the first sub controller 100a, the cool sealing liquid L1 is supplied to the blood pump 400/400a from the second cool sealing liquid reservoir 210 in which the cool sealing liquid L1 is stored (refilled) through the up tube 310.

In the blood pump controller 13 according to the embodiment 3, the second cool sealing liquid reservoir 210 is newly provided between the first pipe joint downstream side 221b and the second pipe joint upstream side 222a in the second sub controller 203. With such a configuration, in addition to "the first liquid replenishing mode" described in 3. (1) of the above-mentioned embodiment 1, the cool sealing liquid L1 stored in the second cool sealing liquid reservoir 210 can also contribute to the supply of the cool sealing liquid to a gap 454 formed between a first slide surface 411 and a second slide surface 421. Accordingly, even if a consumption amount of the cool sealing liquid L1 between the first slide surface 411 and the second slide surface 421 is increased compared to a usual consumption amount (excessive consumption), the cool sealing liquid L1 can be supplied to the gap 454 formed between the first slide surface 411 and the second slide surface 421 over a sufficient period by only the second sub controller 203 and hence, an operation of the blood pump 400/400a can be continued (unnecessary to frequently replenish the cool sealing liquid).

Further, the second cool sealing liquid reservoir 210 can compensate for a function which the cool sealing liquid reservoir 951 performs in the conventional ventricular assist system and hence, unlike the prior art, it is unnecessary to carry the whole cool sealing liquid reservoir 951 having a large size and a large weight.

Further, in the embodiment 3, the capacity of the second cool sealing liquid reservoir 210 is set smaller than the capacity of the first cool sealing liquid reservoir 110. By setting such a capacity ratio between the first cool sealing liquid reservoir 110 and the second cool sealing liquid reservoir 210, in carrying the ventricular assist system by separating only the second sub controller 203, a user carries the second cool sealing liquid reservoir 210 having a relatively small capacity compared to the first cool sealing liquid reservoir 110 and hence, a burden imposed on the user can be further reduced.

Accordingly to the ventricular assist system 3 and the blood pump controller 13 of the embodiment 3, it is possible to provide a ventricular assist system 3 and a blood pump controller 13 which impose a small burden on a user and have high portability.

(2) Other Configurations

The ventricular assist system 3 and the blood pump controller 13 according to the embodiment 3 may further include a germ elimination filters 240, 242 and a one-directional valve 244 in the second sub controller 203, and an ultrafiltration filter 130 in the first sub controller 100a.

By providing the germ elimination filters 240 and 242 at positions close to relay ports of the first pipe joint downstream side 221b and a fourth pipe joint upstream side 224a (appearing in an external field when the second sub controller 203 is separated), undesired matter (germs or the like) can be removed just before the cool sealing liquid L1 flows into a blood pump 400/400a side.

Further, undesired matter which may be contained in the cool sealing liquid can be removed by the ultrafiltration filter 130.

With such a configuration, it is possible to provide more hygienic ventricular assist system 3 and blood pump controller 13.

In selecting the filters, the filters are not limited to so-called germ elimination filters, ultrafiltration filter or the like, and other filters can be selected provided that these filters can achieve a desired object.

(3) The ventricular assist system 3 and the blood pump controller 13 according to the embodiment 3 have substantially the same configuration as the ventricular assist system 1 and the blood pump controller 11 according to the embodiment 1 and the ventricular assist system 2 according to the embodiment 2 except for the configuration of the blood pump controller. Accordingly, the ventricular assist system. 3 and the blood pump controller 13 according to the embodiment 3 acquire the corresponding advantageous effects found amongst all advantageous effects which the ventricular assist system 1 and the blood pump controller 11 according to the embodiment 1 and the ventricular assist system 2 according to the embodiment 2 acquire.

Embodiment 4

Next, a ventricular assist system 4 and a blood pump controller 14 according to the embodiment 4 are described with reference to FIG. 7A and FIG. 7B, FIG. 8, and FIG. 9A and FIG. 9B. The description of constitutional elements of the embodiment 4 which are substantially equal to the corresponding constitutional elements of the embodiments 1 to 3 is omitted.

Figure 7A:
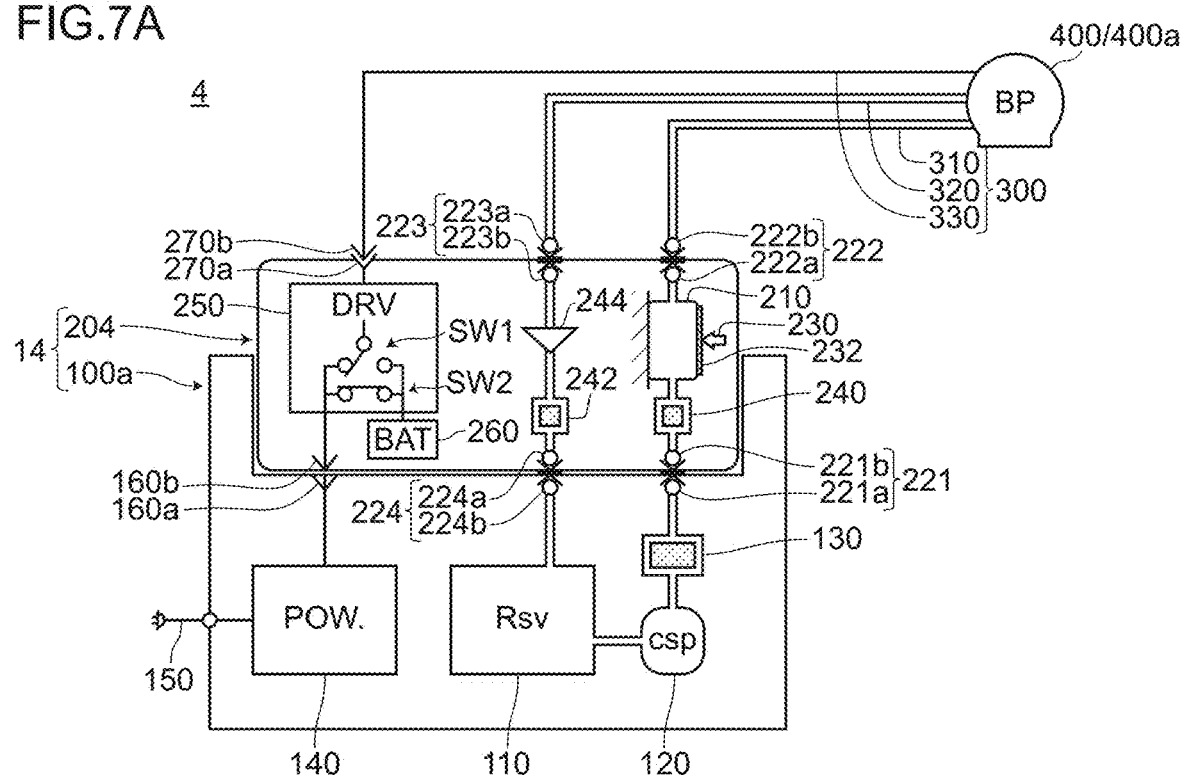
FIG. 7A and FIG. 7B are block diagrams for describing a ventricular assist system 4 and a blood pump controller 14 according to an embodiment 4.
Figure 7B:
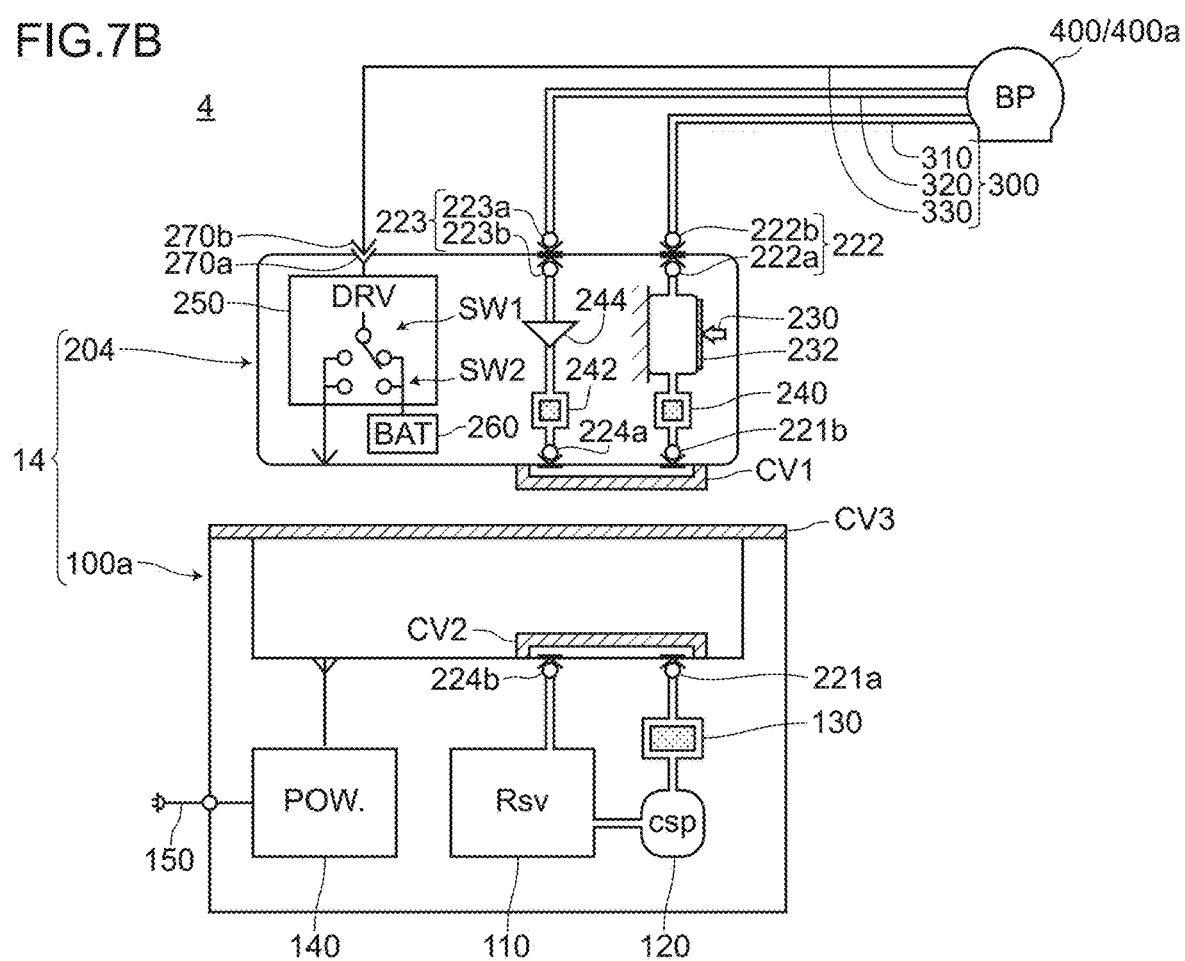
Figure 8:
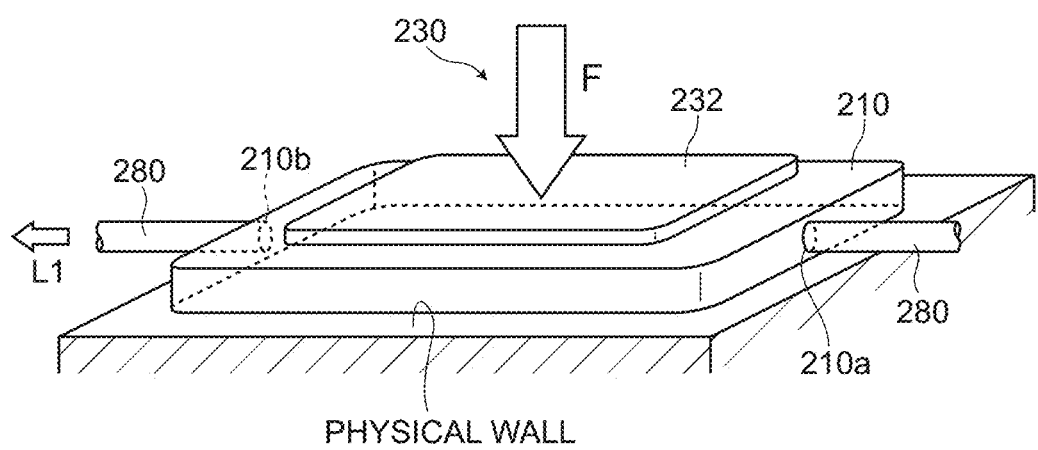
FIG. 8 is a perspective view for describing one example of a second cool sealing liquid reservoir 210 and one example of a pressure applying means 230 according to the embodiment 4.

FIG. 7A and FIG. 7B are block diagrams for describing the ventricular assist system 4 and the blood pump controller 14 according to the embodiment 4. FIG. 7A is a block diagram showing a state where a second sub controller 204 is connected to a first sub controller 100a (a docked state). FIG. 7B is a view showing a state where the second sub controller 204 is separated from the first sub controller 100a. FIG. 8 is a perspective view for describing one example of a second cool sealing liquid reservoir 210 and one example of a pressure applying means 230 according to the embodiment 4.

The ventricular assist system 4 and the blood pump controller 14 according to the embodiment 4 have basically substantially the same configuration as the ventricular assist system 3 and the blood pump controller 13 according to the embodiment 3. However, the ventricular assist system 4 and the blood pump controller 14 according to the embodiment 4 differ from the ventricular assist system 3 and the blood pump controller 13 according to the embodiment 3 with respect to a point that the second sub controller 204 includes a pressure applying means 230.

(1) Pressure Applying Means 230

That is, in the ventricular assist system 4 and the blood pump controller 14 according to the embodiment 4, as shown in FIG. 7A and FIG. 7B, the second sub controller 204 further includes the pressure applying means 230 for increasing a pressure of a cool sealing liquid L1 to be supplied to a blood pump 400/400a.

The pressure applying means 230 may adopt any structure or any method provided that the pressure applying means 230 can increase a pressure of the cool sealing liquid L1 (water pressure) to be supplied to the blood pump 400/400a.

For example, as shown in FIG. 8, the structure may be adopted where a pressure of the cool sealing liquid L1 to be supplied to the blood pump 400/400a is increased by pressing a container of the second cool sealing liquid reservoir 210 with a pressing force F by bringing the container into pressure contact with a physical wall.

Such a structure may further include a pressure applying auxiliary means 232 (the pressure applying auxiliary means 232 being formed of a planar plate in FIG. 8). The pressure applying auxiliary means 232 is brought into contact with a part of a surface of the container of the second cool sealing liquid reservoir 210 so as to transmit the pressing force F to the part of the surface of the container of the second cool sealing liquid reservoir 210.

A supply pressure of the cool sealing liquid L1 can be positively increased by such a pressure applying means 230 and hence, the cool sealing liquid L1 can be more effectively guided between a first slide surface 411 and a second slide surface 421. Eventually, a state of the cool sealing liquid L1 in a gap 454 formed between the first slide surface 411 and the second slide surface 421 can be brought into a state closer to "a preferable state" and hence, the blood pump can be operated safely and with certainty.

The pressure applying means 230 can compensate for a function which the cool sealing liquid pump 952 performs in the conventional ventricular assist system and hence, unlike the prior art, it is unnecessary to carry the cool sealing liquid pump 952 having a large size and a large weight.

The pressure applying means 230 is configured so as to apply a pressure at least when the second sub controller 204 is separated from the first sub controller 100a.

For example, the pressure applying means 230 may be configured so as to apply pressure only when the second sub controller 204 is separated from the first sub controller 100a. The detection of the separation of the second sub controller 204 can be performed using a separation detection means according to an embodiment 5 described later.

For example, the pressure applying means 230 may be configured so as to constantly apply a pressure regardless of separation or connection of the second sub controller 204 with the first sub controller 100a. With such a configuration, a switching mechanism which makes applying of a pressure valid or invalid becomes unnecessary and hence, it is possible to provide the blood pump controller having lower probability of the occurrence of a defect. In this case, during a period that the second sub controller 204 is connected (docked) to the first sub controller 100a, the cool sealing liquid L1 is filled in the second cool sealing liquid reservoir 210 at a pressure equal to or more than a pressure generated by the pressure applying means 230.

(2) External Appearance of Second Cool Sealing Liquid Reservoir 210

It is preferable that the second cool sealing liquid reservoir 210 according to the embodiment 3 or the embodiment 4 have an flattened portion, and have a flat external appearance as a whole as shown in FIG. 8.

In this case, the second cool sealing liquid reservoir 210 may have an approximately rectangular parallelepiped shape. The second cool sealing liquid reservoir 210 may have a cool sealing liquid inflow port 210a to which a pipe 280 is connected at one end side of the second cool sealing liquid reservoir 210, and a cool sealing liquid flowout port 210b to which the pipe 280 is connected at the other end side of the second cool sealing liquid reservoir 210 (FIG. 8).

The second cool sealing liquid reservoir 210 has a flat external appearance as a whole and hence, a size of the second cool sealing liquid reservoir 210 in a thickness direction can be made small whereby a housing of the second sub controller 203/204 in which the second cool sealing liquid reservoir 210 is housed can be made thin. By making the second sub controller 203/204 thin, a user can easily carry and hence, the second sub controller 203/204 has excellent portability.

Further, the second cool sealing liquid reservoir 210 has the flattened portion and hence, the whole surface of the flattened portion can be pressed by making use of the flattened portion. For example, by merely imparting the slight displacement to the second cool sealing liquid reservoir 210 in a direction perpendicular to the surface of the flattened portion by the pressure applying means 230, a volume of the second cool sealing liquid reservoir 210 is relatively largely changed and hence, a pressure of a cool sealing liquid L1 to be supplied to the blood pump 400/400a can be easily increased.

(3) Material of Second Cool Sealing Liquid Reservoir 210

It is preferable that the second cool sealing liquid reservoir 210 according to the embodiment 3 or the embodiment 4 be formed using a material which contains polypropylene or polyethylene.

By forming the second cool sealing liquid reservoir 210 using a material which contains polypropylene or polyethylene, it is possible to acquire the second cool sealing liquid reservoir 210 which is relatively easily deformable (that is, a volume of the second cool sealing liquid reservoir 210 easily changes) and can easily convert a force applied from the pressure applying means 230 to a supply pressure of the cool sealing liquid.

A material which contains polypropylene or polyethylene can be easily formable and light-weighted and hence, it is possible to easily form the second cool sealing liquid reservoir 210 having a small thickness and being light-weighted whereby a burden imposed on a user when the user carries the second sub controller 204 can be reduced.

(4) Specific Example of Pressure Applying Means 230

Figure 9A:
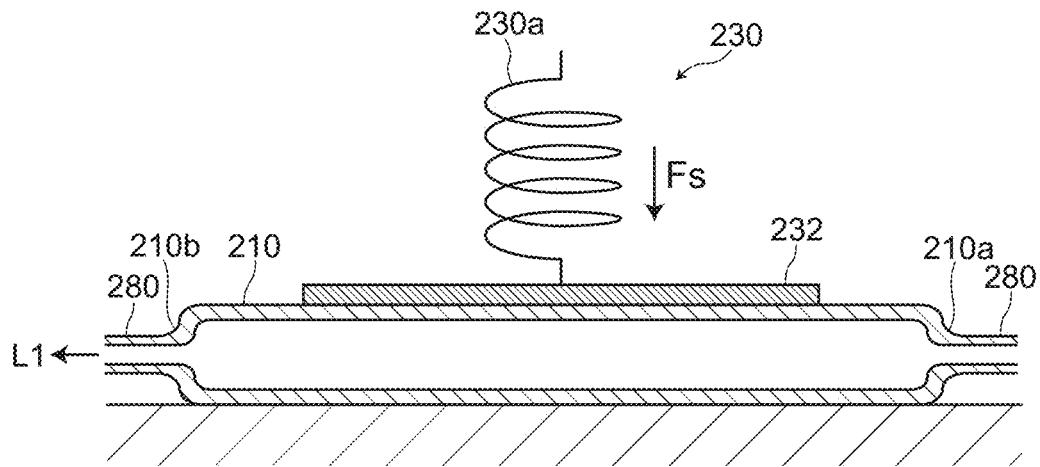
FIG. 9A and FIG. 9B are cross-sectional views for describing the second cool sealing liquid reservoir 210 and the pressure applying means 230 according to the embodiment 4.
Figure 9B:
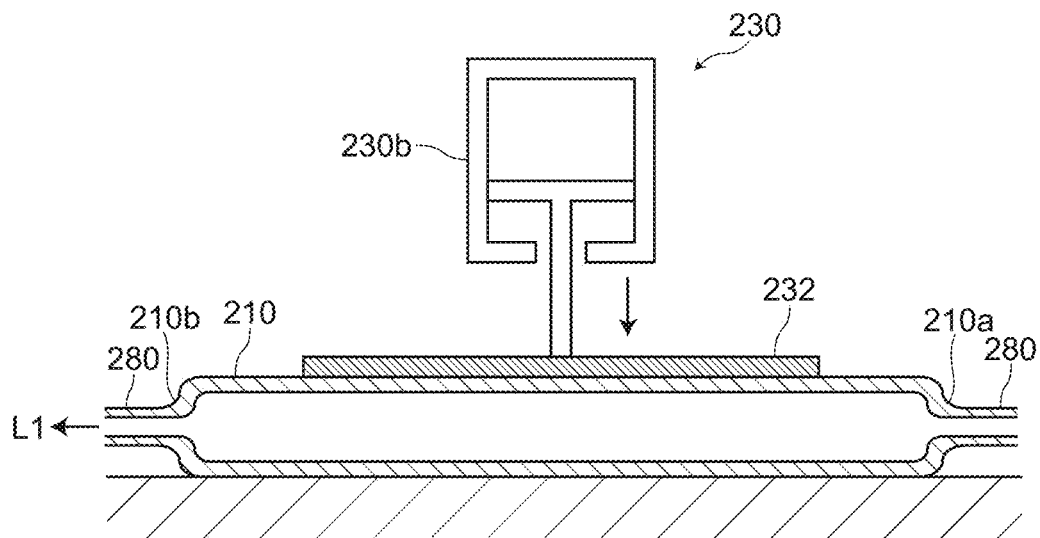

FIG. 9A and FIG. 9B are cross-sectional views for describing the second cool sealing liquid reservoir 210 and the pressure applying means 230 according to the embodiment 4. FIG. 9A is a cross-sectional view showing a mode where a pressure is applied using a pressure applying means (230a) formed of an elastic member. FIG. 9B is a cross-sectional view showing a mode where a pressure is applied using a pressure applying means (230b) formed of an actuator.

As shown in FIG. 9A, it is preferable that the pressure applying means 230 according to the embodiment 4 be an elastic member 230a which applies a force to the second cool sealing liquid reservoir 210.

As the elastic member 230a, a spring member, a sponge or the like can be adopted, for example.

By using the elastic member 230a as the pressure applying means 230, it is possible to acquire the pressure applying means which has small possibility of occurrence of a defect due to the relatively convenient and simple structure.

As shown in FIG. 9B, it is preferable that the pressure applying means 230 according to the embodiment 4 be the actuator 230b which applies a force to the second cool sealing liquid reservoir 210.

The actuator 230b may adopt any device provided that the device is operable by an electrical control. For example, a pneumatic cylinder, a solenoid, a motor, a ball screw, a rack-and-pinion mechanism and the like are considered.

By using the actuator 230b as the pressure applying means 230, it is possible to acquire the pressure applying means where a magnitude of a pressure, a timing at which a pressure is applied, a time during which the pressure is applied and the like can be flexibly controlled.

(5) The ventricular assist system 4 and the blood pump controller 14 according to the embodiment 4 have substantially the same configuration as the ventricular assist system 3 and the blood pump controller 13 according to the embodiment 3 except for a point that the second sub controller includes the pressure applying means 230. Accordingly, the ventricular assist system 4 and the blood pump controller 14 according to the embodiment 4 acquire the corresponding advantageous effects found amongst all advantageous effects which the ventricular assist system 3 and the blood pump controller 13 according to the embodiment 3 acquire.

Embodiment 5

Next, a blood pump controller 15 according to the embodiment 5 is described with reference to FIG. 10A and FIG. 10B. The description of constitutional elements of the embodiment 5 which are substantially equal to the corresponding constitutional elements of the embodiments 1 to 4 is omitted.

Figure 10A:
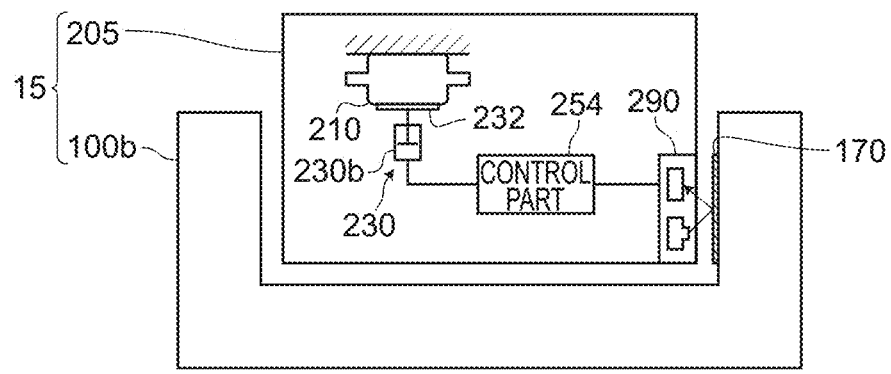
FIG. 10A and FIG. 10B are block diagrams for describing a blood pump controller 15 according to an embodiment 5.
Figure 10B:
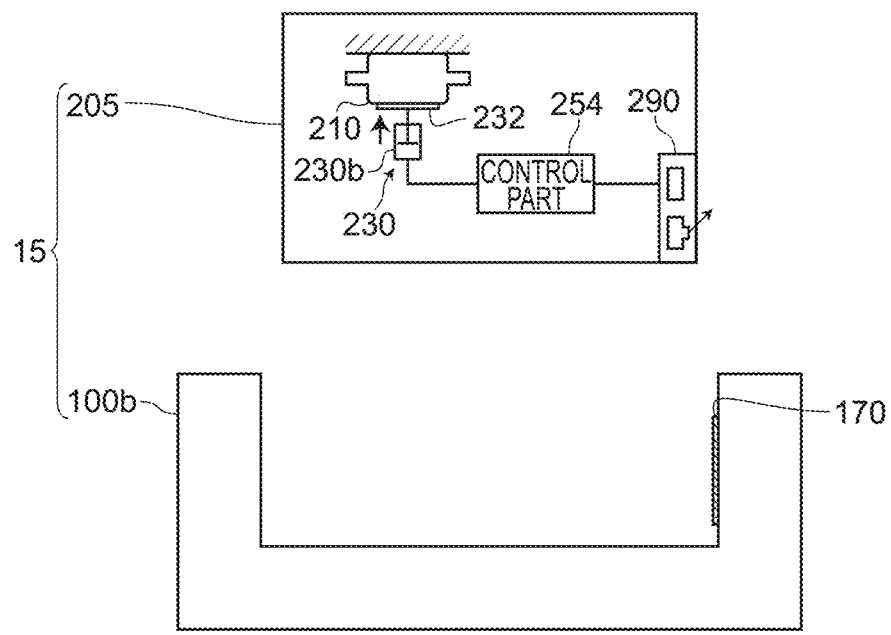

FIG. 10A and FIG. 10B are block diagrams for describing the blood pump controller 15 according to the embodiment 5. FIG. 10A is a block diagram showing a state where a second sub controller 205 is connected to a first sub controller 100b (a docked state). FIG. 10B is a view showing a state where the second sub controller 205 is separated from the first sub controller 100b.

The blood pump controller 15 according to the embodiment 5 has basically substantially the same configuration as the blood pump controllers 11, 12 (not shown in the drawing), 13, and 14 according to the embodiments 1 to 4. However, the blood pump controller 15 according to the embodiment 5 differs from the blood pump controllers 11, 12, 13, and 14 according to the embodiments 1 to 4 with respect to a point that the blood pump controller 15 according to the embodiment 5 has a function of detecting separation between the first sub controller and the second sub controller.

That is, the blood pump controller 15 according to the embodiment 5 further includes a separation detection means (a composite body of a takeout detection sensor 290 and a reflector 170 in FIG. 10A and FIG. 10B) for detecting a separated state and a joined state between the first sub controller 100b and the second sub controller 205.

The separation detection means is mounted on the first sub controller 100b and/or the second sub controller 205, for example. The separation detection means may be configured to detect conduction/non-conduction of a circuit, a change in potential or the like brought about by connection/separation of a mechanical switch, an optical switch or a connector.

For example, as shown in FIG. 10A and FIG. 10B, the separation detection means may be configured such that the takeout detection sensor 290 which has a light emitting part and a light reception part is mounted on an end portion of a housing of the second sub controller 205, and the reflector 170 which reflects light is mounted on a portion of the first sub controller 100b corresponding to the end portion of the housing of the second sub controller 205. When the second sub controller 205 is separated from the first sub controller 100b and is taken out, light emitted from the light emitting part of the takeout detection sensor 290 does not enter the light reception part and hence, the takeout detection sensor 290 detects that the second sub controller 205 is separated and is taken out.

By making use of such a separation detection means, for example, the sequence performed after the first sub controller 100b and the second sub controller 205 are separated from each other and the sequence performed after the first sub controller 100b and the second sub controller 205 are joined to each other can be started at appropriate timing.

As the sequence performed after the first sub controller 100b and the second sub controller 205 are separated from each other, for example, a control of connecting a first switch SW1 to a battery 260 side, the start of applying a pressure by a pressure applying means, a control of a time used in a state the second sub controller is separated after starting counting up of a timer from a point of time of separation and the like are named.

As the sequence performed after the first sub controller 100b and the second sub controller 205 are joined to each other, for example, a control of connecting the first switch SW1 to a power source circuit 140 side, the cessation of applying a pressure by the pressure applying means and the like are named.

The blood pump controller 15 according to the embodiment 5 has substantially the same configuration as the blood pump controllers 11, 12, 13, and 14 according to the embodiments 1 to 4 except for a point that the blood pump controller 15 according to the embodiment 5 has a function of detecting separation between the first sub controller and the second sub controller. Accordingly, the blood pump controller 15 according to the embodiment 5 acquires the corresponding advantageous effects found amongst all advantageous effects which the blood pump controllers 11, 12, 13, and 14 according to the embodiments 1 to 4 acquire.

Example

An example in which the ventricular assist system and the blood pump controller according to the present invention were carried out is described hereinafter.
(1) Blood Pump and Blood Pump Controller According to Example The blood pump 400a according to the embodiment 2 was manufactured as a prototype, and this blood pump 400a was set as the blood pump according to the example. The blood pump controller 14 according to the embodiment 4 was manufactured as a prototype, and this blood pump controller 14 was set as the blood pump controller according to the example.

A size of the blood pump controller according to the example has a size of approximately A4 paper as viewed in a plan view.

Capacity of the first cool sealing liquid reservoir was set to approximately 1000 cc, and capacity of the second cool sealing liquid reservoir was set to approximately 10 cc to 100 cc. A weight of the first sub controller was set to approximately 2.3 kg to 3.7 kg, and a weight of the second sub controller was set to approximately 300 g to 700 g.
(2) Blood Pump and Blood Pump Controller According to Comparison Example A size of the blood pump controller according to the comparison example was also set to a size of approximately A4 paper as viewed in a plan view.

The blood pump 400a according to the embodiment 2 was set as the blood pump according to the comparison example. With respect to a blood pump controller, the conventional blood pump controller 19 was set as the blood pump controller according to the comparison example.

In the blood pump controller according to the comparison example, capacity of a cool sealing liquid reservoir was approximately 1000 cc. A weight of the whole blood pump controller was approximately 3 kg to 4 kg.
(3) Advantageous Effects Acquired by Blood Pump and Blood Pump Controller According to Example In the example, it was assumed that an average consumption amount per day of a cool sealing liquid in the blood pump is approximately 1 cc to 7 cc, and a second cool sealing liquid reservoir was a reservoir having capacity of approximately 10 cc to 100 cc. It was confirmed that according to the blood pump and the blood pump controller of the example, the blood pump is operable at least one day or more only by the second sub controller, and the blood pump controller has sufficient basic ability assuming that the user goes out for a simple walk or the like.

A size of the second sub controller was approximately A6 paper as viewed in a plan view. A weight of the second sub controller was 300 g to 700 g. From the above, it was confirmed that the blood pump controller according to the example is a blood pump controller which is small sized and light weighted to an extent that a user can wear and use the blood pump controller on his body (for example, to an extent that the user can carry by attaching the blood pump controller on his waist, for example).

As has been described above, in the blood pump and the blood pump controller (second sub controller) according to the present invention, it is sufficient to carry only the second sub controller which is small sized and light-weighted without carrying the first cool sealing liquid reservoir having capacity of 1000 cc. Accordingly, it was confirmed that the blood pump controller according to the present invention is a blood pump controller which imposes small burden on a user and has high portability enabling a user to carry the second sub controller relatively easily.

Although the present invention has been described based on the above-mentioned embodiments, the present invention is not limited to the above-mentioned embodiments, and the present invention can be carried out without departing from the gist of the present invention, for example, the following modifications are also conceivable.
(1) The numbers, the materials, the shapes, the positions, the sizes, the angles and the like of the constitutional elements described in the above-mentioned respective embodiments are provided only for an exemplifying purpose, and these can be changed within ranges where advantageous effects of the present invention are not impaired.

(2) In the respective embodiments, after the second sub controller is separated from the first sub controller, the first pipe joint downstream side 221b and the fourth pipe joint upstream side 224a of the second sub controller are basically in a released state although the relay ports are shut off or these sides are protected by the cover. However, the present invention is not limited to such a configuration. For example, the first pipe joint downstream side and the fourth pipe joint upstream side may be connected to each other by a pipe or the like.

By connecting the first pipe joint downstream side 221b and the fourth pipe joint upstream side 224a by the pipe or the like, the cool sealing liquid L1 returned from the blood pump through the down tube 320 can be supplied to the blood pump side through the up tube 310 again. Further, the relay ports of the first pipe joint downstream side 221b and the fourth pipe joint upstream side 224a do not appear in an external field and hence, the intrusion of foreign substances, germs and the like from the external field to the inside can be prevented.

(3) In the mode shown in FIG. 4A to FIG. 4D of the embodiment 2, the dynamic pressure grooves 460 are formed of grooves formed on the second slide surface 421 of the rotary side slide member 422. However, the present invention is not limited to such a configuration.

Figure 11:
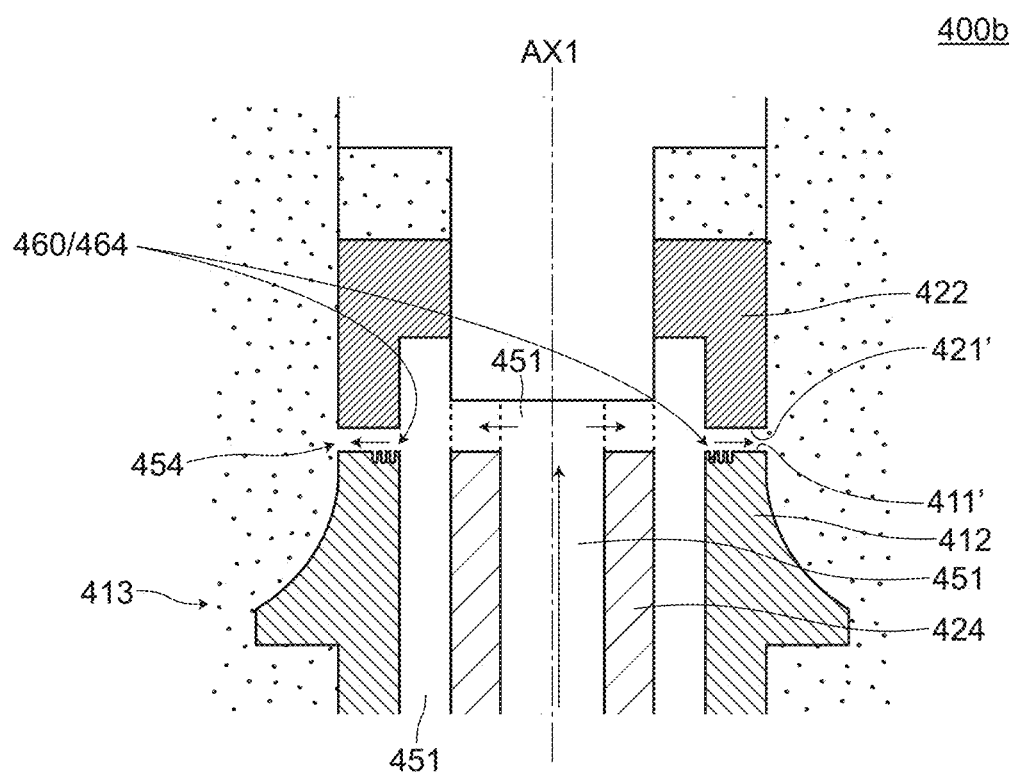
FIG. 11 is a cross-sectional view of a main part for describing a blood pump 400b according to a modification 1.

FIG. 11 is a cross-sectional view of a main part for describing a blood pump 400b according to a modification 1.

For example, as shown in FIG. 11, dynamic pressure grooves 460 may be formed of grooves formed on a first slide surface 411' of a fixed side slide member 412 (the dynamic pressure grooves 464 in modification 1).

(4) In the embodiment 2, the dynamic pressure grooves 460 are formed of grooves formed on the first slide surface 411 of the fixed side slide member 412 or the second slide surface 421 of the rotary side slide member 422. However, the present invention is not limited to such a configuration. For example, the dynamic pressure grooves 460 may be formed of grooves formed on a shaft 424' connected to a motor 440 or a bearing 413 (modification 2).

Figure 12A:
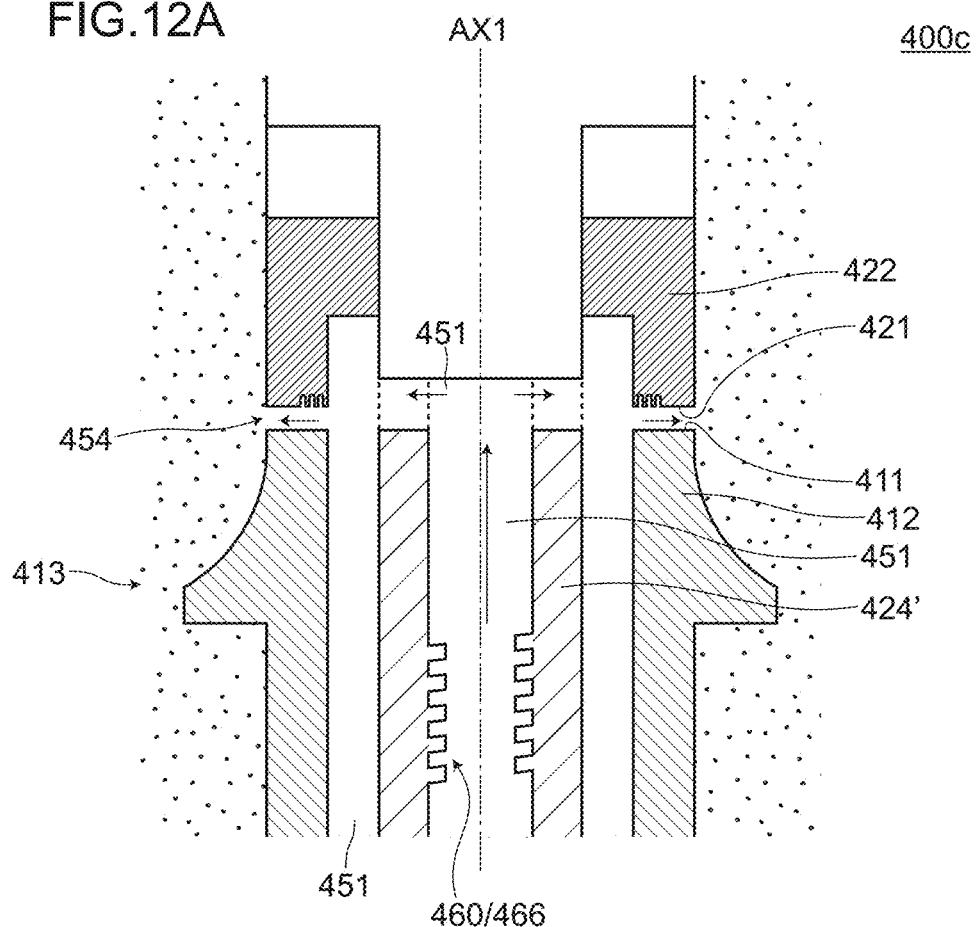
FIG. 12A and FIG. 12B are views for describing a blood pump 400c according to a modification 2.
Figure 12B:
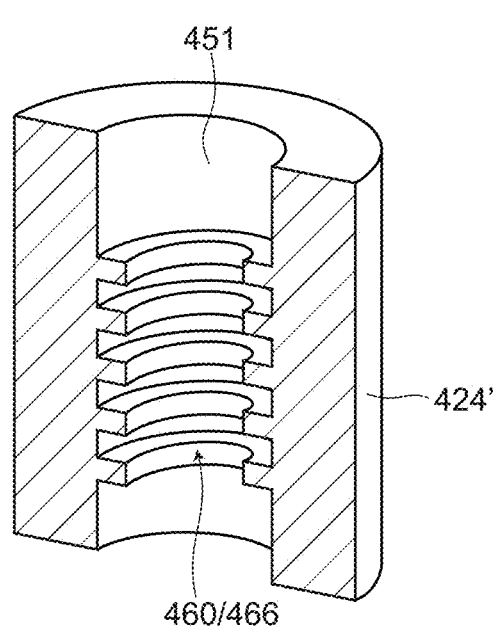

FIG. 12A and FIG. 12B are views for describing a blood pump 400c according to a modification 2. FIG. 12A is a cross-sectional view of a main part of the blood pump 400c. FIG. 12B is a perspective view showing a cross section of a shaft 424' taken along a rotary axis AX1 of the motor and showing the inside of the shaft 424'.

For example, as shown in FIG. 12A and FIG. 12B, dynamic pressure grooves 460 are formed of grooves formed on the shaft 424' connected to the motor 440 (the dynamic pressure grooves 466 of modification 2). Although an example is illustrated where the grooves are formed on an inner side of the shaft 424' having a circular cylindrical shape, the grooves may be formed on an outer side of the shaft 424' (not shown in the drawing). By forming the dynamic pressure grooves 460 on the outer side of the shaft 424' than the inner side of the shaft 424', the dynamic pressure grooves can be easily formed from a viewpoint of restricting a space and at the same time, from a viewpoint of forming the dynamic pressure grooves 460.

By forming the dynamic pressure grooves on at least either one of the shaft or the bearing which are relatively rotatable to each other, it is possible to impart a dynamic pressure effect to the cool sealing liquid L1 which passes between the shaft and the bearing. As a result, it is possible to more effectively guide the cool sealing liquid to the gap 454 formed between the first slide surface 411 and the second slide surface 421.

The dynamic pressure grooves 460 may be simply formed on only the shaft or the bearing, or may be formed on the first slide surface 411 or the second slide surface 421 as well as on the shaft or the bearing as shown in FIG. 12A and FIG. 12B.

(5) In the embodiment 4, as the specific example of the pressure applying means 230, the configuration is exemplified where the container of the second cool sealing liquid reservoir 210 is brought into pressure contact with the physical wall so that a pressing force F is applied to the container in a direction perpendicular to the physical wall using the pressure applying auxiliary means 232 (the planar plate in this embodiment) (see FIG. 8). However, the present invention is not limited to such a configuration. For example, the configuration may be adopted where a pressure of the cool sealing liquid L1 (water pressure) is increased by adding a force in a direction parallel to the physical wall.

Figure 13A:
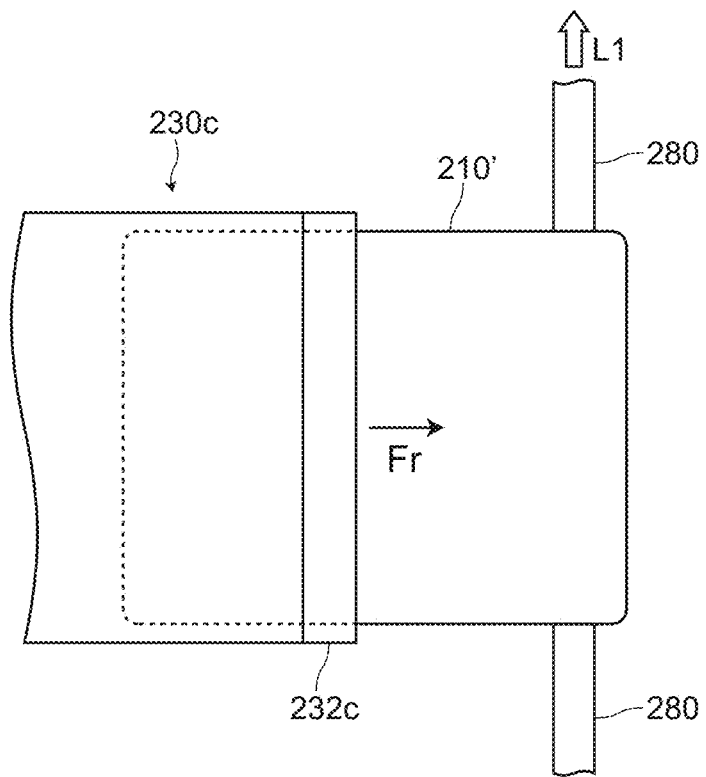
FIG. 13A and FIG. 13B are views for describing a second cool sealing liquid reservoir 210' and a pressure applying means 230c according to a modification 3.
Figure 13B:
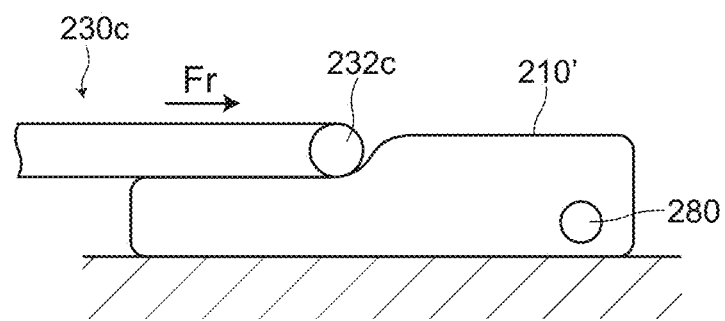
Figure 14A:
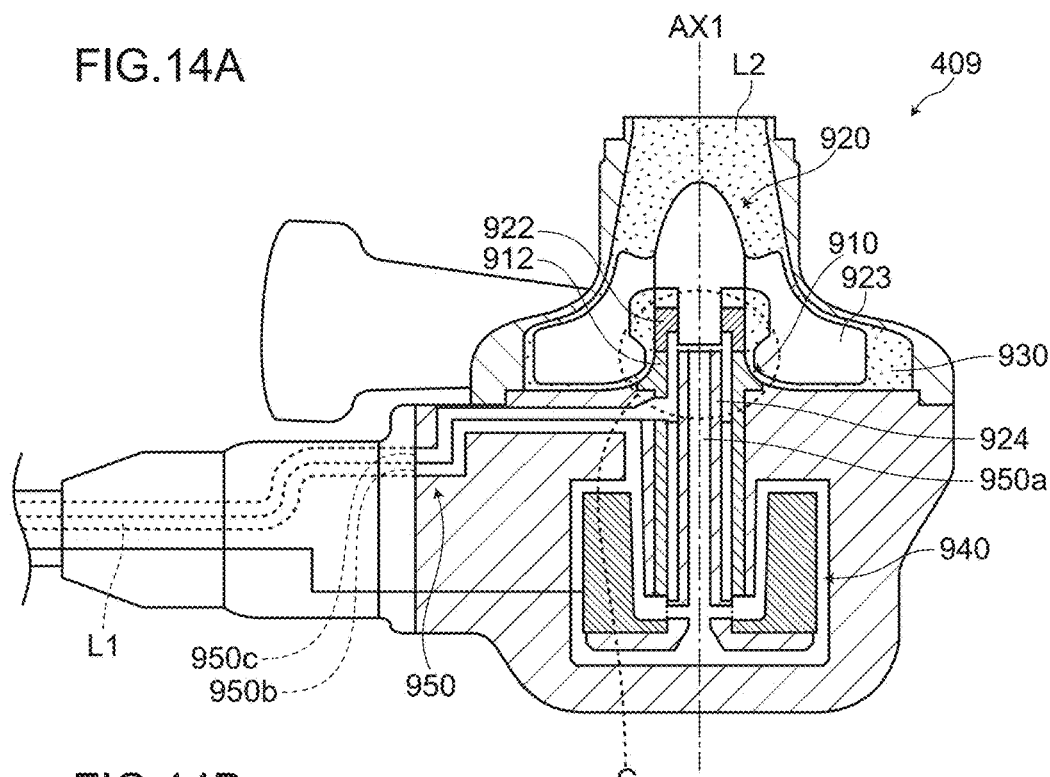
FIG. 14A to FIG. 14C are views for describing one example of a centrifugal type blood pump 409.
Figure 14B:
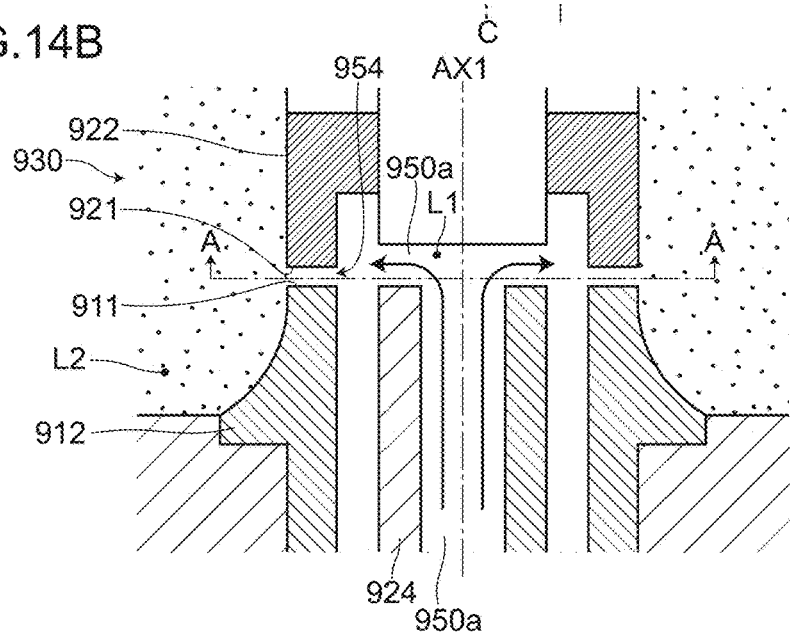
Figure 14C:
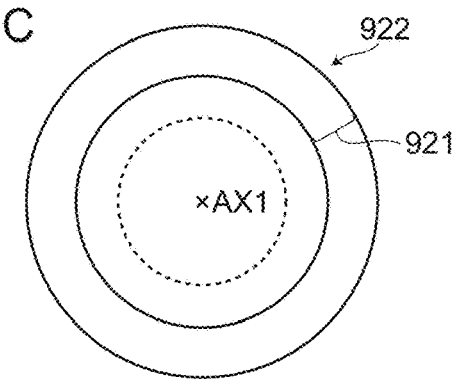
Figure 15:
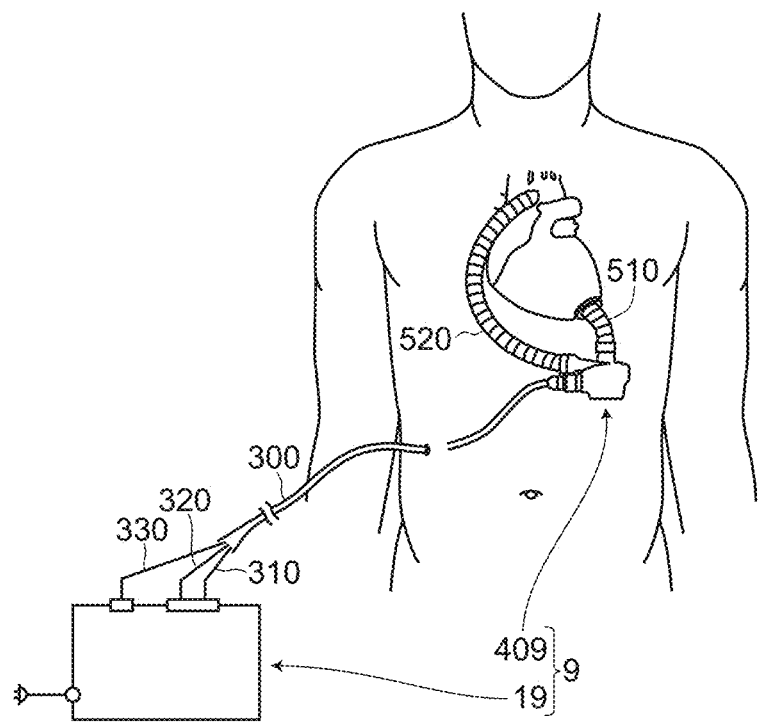
FIG. 15 is a schematic view for describing a conventional ventricular assist system 9 and a conventional blood pump controller 19.
Figure 16:
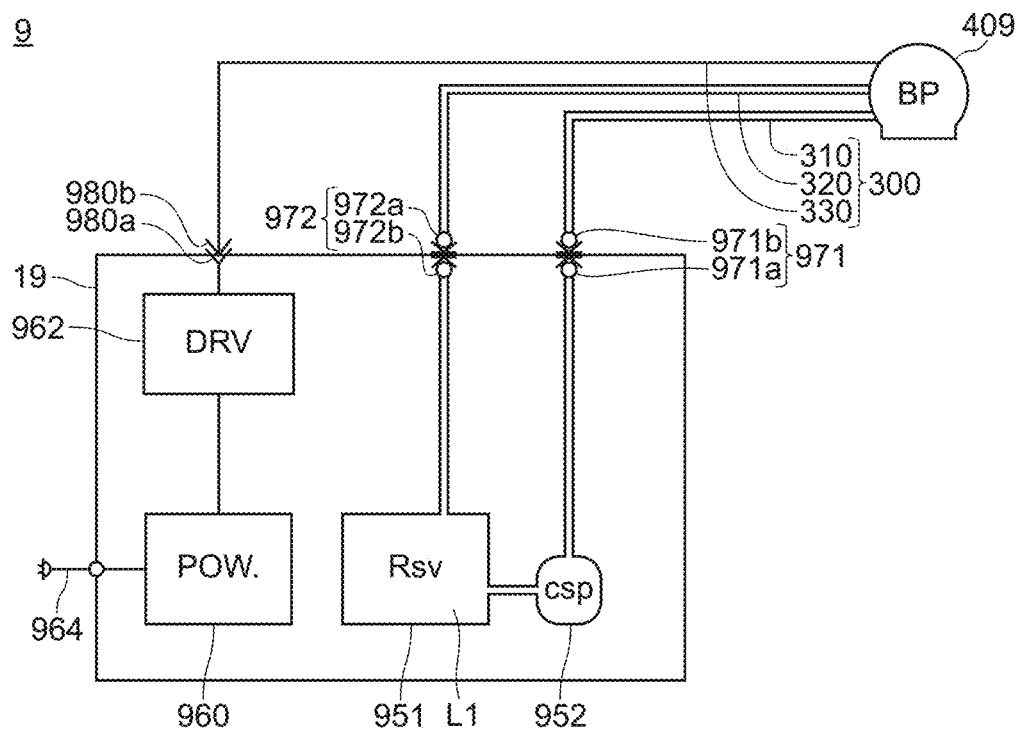
FIG. 16 is a block diagram for describing the conventional ventricular assist system 9 and the conventional blood pump controller 19.

FIG. 13A and FIG. 13B are views for describing a second cool sealing liquid reservoir 210' and a pressure applying means 230c according to a modification 3. FIG. 13A is a plan view of the second cool sealing liquid reservoir 210' and the pressure applying means 230c. FIG. 13B is a cross-sectional view of the second cool sealing liquid reservoir 210' and the pressure applying means 230c.

As shown in FIG. 13A and FIG. 13B, the second cool sealing liquid reservoir 210' and the pressure applying means 230c of the modification 3 adopt the configuration where a pressure of a cool sealing liquid L1 (water pressure) is increased by adding a force Fr from the pressure applying means 230c (a roller in this modification) to the second cool sealing liquid reservoir 210' in a direction parallel to a physical wall.

With such a configuration, a direction of a stroke of a means which imparts a force is parallel to the physical wall and hence, the means which imparts a force is housed in a planar direction in FIG. 13A and in a longitudinal direction in FIG. 13B. Accordingly, a housing of the second sub controller can be made small-sized.

(6) The second sub controllers 203, 204 of the embodiments 3 and 4 may be configured such that, when the second sub controllers 203, 204 are separated from the first sub controller 100a, a cool sealing liquid flow path between the second cool sealing liquid reservoir 210 and the germ elimination filter 240 and a cool sealing liquid flow path between the one-directional valve 244 and the germ elimination filter 242 are shut off respectively.

With such a configuration, even in a state where the second sub controllers 203, 204 are separated, it is possible to prevent foreign substances trapped by germ elimination filters 240, 242 from moving toward a second cool sealing liquid reservoir 210 side and a one-directional valve 244 side.

(7) The blood pumps 400 of the above-mentioned respective embodiments have been described on the premise of the so-called centrifugal type blood pump. However, the present invention is not limited to such a centrifugal type blood pump. The present invention may be carried out on the premise of, for example, an axial blood pump having slide surface (a mechanical seal) which requires the supply of a cool sealing liquid.

What is claimed is:

1. A ventricular assist system comprising:
a blood pump having: a fixed side slide member having an annular first slide surface; a rotary side slide member having an annular second slide surface; a blood pump chamber positioned on an outer peripheral side of the fixed side slide member and the rotary side slide member, an impeller housed in the blood pump chamber and being integrally rotatable with the rotary side slide member; a motor capable of imparting rotary energy to the impeller; and a cool sealing liquid flow chamber which is positioned on an inner peripheral side of the fixed side slide member and the rotary side slide member and through which a cool sealing liquid supplied from an outside flows, the blood pump being used in a state where the first slide surface and the second slide surface are brought into contact with each other, and the cool sealing liquid is supplied to a gap formed between the first slide surface and the second slide surface from the cool sealing liquid flow chamber;
a blood pump controller for driving the blood pump and for supplying the cool sealing liquid to the blood pump;
an electric cable for transmitting a drive signal from the blood pump controller to the blood pump;
an up tube through which the cool sealing liquid is made to flow from the blood pump controller to the blood pump; and
a down tube through which the cool sealing liquid is made to flow from the blood pump to the blood pump controller, wherein
the blood pump controller includes:
a blood pump drive circuit electrically connected to the electric cable and provided for driving the motor of the blood pump;
a battery electrically connected to the blood pump drive circuit for supplying a power source to the blood pump drive circuit;
a first cool sealing liquid reservoir for storing the cool sealing liquid;
a cool sealing liquid pump for sucking the cool sealing liquid supplied from the first cool sealing liquid reservoir and discharging the sucked cool sealing liquid;
a first pipe joint formed of a first pipe joint upstream side and a first pipe joint downstream side which are detachably connected to each other and being capable of relaying the cool sealing liquid supplied from the cool sealing liquid pump;
a second pipe joint formed of a second pipe joint upstream side and a second pipe joint downstream side which are detachably connected to each other where the second pipe joint downstream side is connected to the up tube so as to enable the second pipe joint to relay the cool sealing liquid supplied from the first pipe joint to the up tube;
a third pipe joint formed of a third pipe joint upstream side and a third pipe joint downstream side which are detachably connected to each other where the third pipe joint upstream side is connected to the down tube so as to enable the third pipe joint to relay the cool sealing liquid supplied from the down tube to an inside of the blood pump controller; and
a fourth pipe joint formed of a fourth pipe joint upstream side and a fourth pipe joint downstream side which are detachably connected to each other and being capable of relaying the cool sealing liquid supplied from the third pipe joint downstream side to the first cool sealing liquid reservoir, and the blood pump controller includes:
a first sub controller (home station) having the first cool sealing liquid reservoir, the cool sealing liquid pump, the first pipe joint upstream side, and the fourth pipe joint downstream side; and
a second sub controller (a portable side controller) having the blood pump drive circuit, the battery, the first pipe joint downstream side, the second pipe joint upstream side, the third pipe joint downstream side, and the fourth pipe joint upstream side, and
the first sub controller and the second sub controller are separable from each other and are joinable to each other by detachably connecting the first pipe joint and the fourth pipe joint.

2. The ventricular assist system according to claim 1, wherein the first pipe joint upstream side, the first pipe joint downstream side, the fourth pipe joint upstream side, and the fourth pipe joint downstream side respectively include a relay port shut off means which is disposed in a vicinity of a relay port which appears when a pipe joint of each of said respective sides is separated from a pipe joint of a counterpart side which forms a pair with said each of the sides and shuts off between an outer portion and an inner portion of the relay port.

3. The ventricular assist system according to claim 1, wherein in the blood pump, a dynamic pressure groove is formed on a member which forms a part of a cool sealing liquid flow path.

4. The ventricular assist system according to claim 3, wherein the dynamic pressure groove is a groove formed on the first slide surface of the fixed side slide member or the second slide surface of the rotary side slide member.

5. The ventricular assist system according to claim 3, wherein the dynamic pressure groove is a groove formed on a shaft connected to the motor or a bearing.

6. A blood pump controller being the blood pump controller used in the ventricular assist system according to claim 1, the blood pump controller comprising:
the blood pump drive circuit electrically connected to the electric cable and provided for driving the motor of the blood pump;
the battery electrically connected to the blood pump drive circuit for supplying a power source to the blood pump drive circuit;
the first cool sealing liquid reservoir for storing the cool sealing liquid;
the cool sealing liquid pump for sucking the cool sealing liquid supplied from the first cool sealing liquid reservoir and discharging the sucked cool sealing liquid;
the first pipe joint formed of the first pipe joint upstream side and the first pipe joint downstream side which are detachably connected to each other and being capable of relaying the cool sealing liquid supplied from the cool sealing liquid pump;
the second pipe joint formed of the second pipe joint upstream side and the second pipe joint downstream side which are detachably connected to each other where the second pipe joint downstream side is connected to the up tube so as to enable the second pipe joint to relay the cool sealing liquid supplied from the first pipe joint to the up tube;
the third pipe joint formed of the third pipe joint upstream side and the third pipe joint downstream side which are detachably connected to each other where the third pipe joint upstream side is connected to the down tube so as to enable the third pipe joint to relay the cool sealing liquid supplied from the down tube to an inside of the blood pump controller; and the fourth pipe joint formed of the fourth pipe joint upstream side and the fourth pipe joint downstream side which are detachably connected to each other and being capable of relaying the cool sealing liquid supplied from the third pipe joint downstream side to the first cool sealing liquid reservoir, and the first sub controller having the first cool sealing liquid reservoir, the cool sealing liquid pump, the first pipe joint upstream side, the fourth pipe joint downstream side and the second sub controller having the blood pump drive circuit, the battery, the first pipe joint downstream side, the second pipe joint upstream side, the third pipe joint downstream side, and the fourth pipe joint upstream side are separable from each other and are joinable with each other by detachably connecting the first pipe joint and the fourth pipe joint.

7. The blood pump controller according to claim 6, wherein the second sub controller further includes a second cool sealing liquid reservoir disposed between the first pipe joint downstream side and the second pipe joint upstream side, having capacity smaller than capacity of the first cool sealing liquid reservoir, and storing the cool sealing liquid.

8. The blood pump controller according to claim 7, wherein the second sub controller further includes a pressure applying means for increasing a pressure of the cool sealing liquid to be supplied to the blood pump.

9. The blood pump controller according to claim 8, wherein the pressure applying means is an elastic member which applies a force to the second cool sealing liquid reservoir.

10. The blood pump controller according to claim 8, wherein the pressure applying means is an actuator which applies a force to the second cool sealing liquid reservoir.

11. The blood pump controller according to claim 7, wherein the second cool sealing liquid reservoir has an flattened portion, and has a flat external appearance as a whole.

12. The blood pump controller according to claim 7, wherein the second cool sealing liquid reservoir is formed using a material which contains polypropylene or polyethylene.

13. The blood pump controller according to claim 6, further comprising a separation detection means for detecting a separated state and a joined state between the first sub controller and the second sub controller.

* * * * *